(12) United States Patent
Jolidon et al.

(10) Patent No.: US 7,265,126 B2
(45) Date of Patent: Sep. 4, 2007

(54) DIAZA-SPIROPIPERIDINE DERIVATIVES

(75) Inventors: Synese Jolidon, Blauen (CH); Emmanuel Pinard, Linsdorf (FR); Andrew William Thomas, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 424 days.

(21) Appl. No.: 11/028,125

(22) Filed: Jan. 3, 2005

(65) Prior Publication Data
US 2005/0154000 A1 Jul. 14, 2005

(30) Foreign Application Priority Data
Jan. 8, 2004 (EP) ................... 04100034

(51) Int. Cl.
*A61K 31/438* (2006.01)
*C07D 471/10* (2006.01)

(52) U.S. Cl. ............... 514/278; 546/16; 546/15
(58) Field of Classification Search ............... 546/16, 546/15; 540/596; 514/278
See application file for complete search history.

(56) References Cited

U.S. PATENT DOCUMENTS 6,645,973 B1  11/2003  Gibson et al.

FOREIGN PATENT DOCUMENTS

| WO | WO94/13678 A1 | 6/1994 |
| WO | WO97/37630 A2 | 10/1997 |
| WO | WO 03/053942 A1 | 7/2003 |

OTHER PUBLICATIONS

Lewis, D. A. et al., Neuron, 2000, vol. 28 pp. 325-334.
Vandenberg R. J., et al., Exp. Opin. Ther. Targets, 2001, vol. 5(4) pp. 507-518.
Nakazato A. et al., 2000, Exp. Opin. Ther. Patents vol. 10(1) pp. 75-98.
Sharma T., Br. J. Psychiatry, 1999, vol. 174 (Suppl. 28) pp. 44-51.
Javitt D.C., 1999, Biol. Psychiatry, vol. 45, pp. 668-679.
Mohn, A. R. et al., 1999, Cell, vol. 98, pp. 427-436.
Bliss, T. V. et al., 1993, Nature, vol. 361 pp. 31-39.
Tang J. P. et al., 1999, Nature, vol. 401, pp. 63-69.
Gainetdinov R. R. et al., 2002, Trends in Pharm. Sci. vol. 23(8) pp. 367-373.
Lopez-Corcuera B. et al., 2001, Mol. Mem. Biol. vol. 18, pp. 13-20.
Bergeron R. et al., 1998, Proc. Natl. Acad. Sci. USA, vol. 95, pp. 15730-15734.
Chen, L. et al., 2003, J. Neurophysiol. vol. 89(2) pp. 691-703.
Armer R. E. et al., 2001, Exp. Opin. Ther. Patents vol. 11(4) pp. 563-572.
Pralong E. T. et al., 2002, Prog. Neurobiol. vol. 67, pp. 173-202.
Carlsson M. L. 1998, J. Neurol. Transm. vol. 105, pp. 525-535.

*Primary Examiner*—Charanjit S. Aulakh
(74) *Attorney, Agent, or Firm*—George W. Johnston; Patricia S. Rocha-Tramaloni; Kimberly J. Prior

(57) ABSTRACT

The present invention relates to compounds of formula

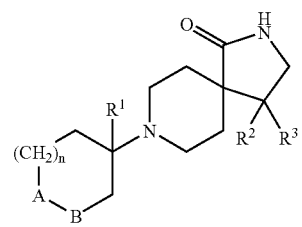

I wherein
A-B, $R^1$, $R^2$,
$R^3$, $R^4$, and n are as defined herein; and to pharmaceutically acceptable salts thereof.

The compounds of formula I may be used in the treatment of neurological and neuropsychiatric disorders.

41 Claims, No Drawings

DIAZA-SPIROPIPERIDINE DERIVATIVES

FIELD OF THE INVENTION

The present invention relates to the treatment of CNS disorders such as schizophrenia and Alzheimer's disease. More particularly, the invention relates to inhibition of GlyT-1.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 2000, 28:325-33). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 2001, 5(4): 507-518; Nakazato A and Okuyama S, et al., 2000, Exp. Opin. Ther. Patents, 10(1): 75-98). This pharmacological approach poorly address negative and cognitive symptoms which are the best predictors of functional outcome (Sharma T., Br. J. Psychiatry, 1999, 174(suppl. 28): 44-51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., 1999, Biol. Psychiatry, 45: 668-679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., 1999, Cell, 98: 427-236).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb D O, 1949, The organization of behavior, Wiley, N.Y.; Bliss T V and Collingridge G L, 1993, Nature, 361: 31-39). Transgenic mice overexpressing the NMDA NR2B subunit exhibit enhanced synaptic plasticity and superior ability in learning and memory (Tang J P et al., 1999, Nature: 401-63-69).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, 2002, Trends in Pharm. Sci., 23(8): 367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, Mol. Mem. Biol., 18: 13-20). Thus, one strategy to enhance NMDA receptor activity is to elevate the glycine concentration in the local microenvironment of synaptic NMDA receptors by inhibition of GlyT-1 transporter (Bergereon R. Et al., 1998, Proc. Natl. Acad. Sci. USA, 95: 15730-15734; Chen L et al., 2003, J. Neurophysiol., 89 (2): 691-703).

Glycine transporters inhibitors are suitable for the treatment of neuroligical and neuropsychiatric disorders. The majority of diseases states implicated are psychoses, schizophrenia (Armer R E and Miller D J, 2001, Exp. Opin. Ther. Patents, 11 (4): 563-572), psychotic mood disorders such as severe major depressive disorder, mood disorders associated with psychotic disorders such as acute mania or depression associated with bipolar disorders and mood disorders associated with schizophrenia, (Pralong E T et al., 2002, Prog. Neurobiol., 67: 173-202), autistic disorders (Carlsson M L, 1998, J. Neural Transm. 105: 525-535), cognitive disorders such as dementias, including age related dementia and senile dementia of the Alzheimer type, memory disorders in a mammal, including a human, attention deficit disorders and pain (Armer R E and Miller D J, 2001, Exp. Opin. Ther. Patents, 11 (4): 563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I

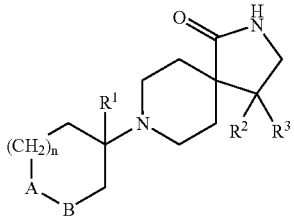

wherein
A-B is CH$_2$—CH$_2$, —CH$_2$—O—, —O—CH$_2$—, —CH$_2$—S—, —S—CH$_2$—, —CH$_2$—C(O)—, —C(O)—CH$_2$—, —N(R$^4$)—CH$_2$— or —CH$_2$—N(R$^4$)—;

R$^1$ is lower alkyl, lower alkenyl, cycloalkyl, or is aryl, optionally substituted by one or two substituents selected from the group consisting of halogen, cyano, lower alkyl, CF$_3$, OCF$_3$ and lower alkoxy, or is heteroaryl, optionally substituted by one or two substituents selected from the group consisting of halogen, lower alkyl, CF$_3$ and lower alkoxy;

R$^2$ is lower alkyl, cycloalkyl, or is aryl, optionally substituted by one or two substituents selected from the group consisting of halogen, lower alkyl, CF$_3$, and lower alkoxy, or is heteroaryl, optionally substituted by one or two substituents selected from the group consisting of halogen, lower alkyl, CF$_3$ and lower alkoxy;

R$^3$ is hydrogen, lower alkyl or benzyl;

R$^4$ is hydrogen or benzyl; and n is 0, 1 or 2;

r a pharmaceutically acceptable salt thereof.

Furthermore, the invention includes all racemic mixtures, all their corresponding enantiomers and/or optical isomers.

The invention also provides processes for the manufacture of compounds of the invention, their enantiomers, and pharmaceutically acceptable salts. The invention further provides pharmaceutical compositions containing an effective amount of one or more compounds of formula I per se, or pharmaceutically acceptable salts thereof, and a pharmaceutically acceptable carrier and method for the manufacture of such compositions.

It has surprisingly been found that the compounds of the invention are good inhibitors of the glycine transporter 1 (GlyT-1), and that they have a good selectivity to glycine transporter 2 (GlyT-2) inhibitors. Thus, the compounds of the invention are useful for the treatment of diseases related to activation of NMDA receptors via Glyt-1 inhibition.

The present invention relates to the treatment of neurological and neuropsychiatric disorders with compounds of the invention. For example, the present invention provides methods for the treatment, control, or prevention of illnesses such as psychoses, disfunction in memory and learning, schizophrenia, dementia and other diseases in which cognitive processes are impaired, such as attention deficit disorders or Alzheimer's disease.

The preferred indications using the compounds of the present invention are schizophrenia, cognitive impairment and Alzheimer's disease.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkenyl" denotes an unsaturated straight- or branched-chain group containing from 2 to 7 carbon atoms with at least one double bond.

The term "cycloalkyl" denotes a saturated or partially saturated ring containing from 3 to 7 carbon atoms, for example cyclopropyl, cyclopentyl, cyclopentenyl, cyclohexyl, cyclohexenyl, cycloheptyl or cycloheptenyl.

The term "halogen" denotes chlorine, iodine, fluorine and bromine.

The term "aryl" denotes a monovalent cyclic aromatic hydrocarbon radical consisting of one or more fused rings in which at least one ring is aromatic in nature, for example phenyl or naphthyl.

The term "heteroaryl" denotes a cyclic aromatic hydrocarbon radical, containing one, two or three heteroatoms, selected from the group consisting of oxygen, sulphur or nitrogen, for example pyridyl, pyrazinyl, pyrimidinyl, pyridazinyl, triazinyl, thiazolyl, thienyl, flryl, pyrrolyl, imidazolyl, pyrazolyl, oxazolyl, isothiazolyl or isoxazolyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salts" embraces salts with inorganic and organic acids, such as hydrochloric acid, nitric acid, sulfuiric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The present invention provides compounds of formula I

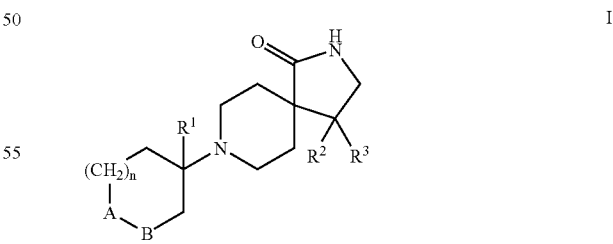

wherein
A-B is CH$_2$—CH$_2$, —CH$_2$—O—, —O—CH$_2$—, —CH$_2$—S—, —S—CH$_2$—, —CH$_2$—C(O)—, —C(O)—CH$_2$—, —N(R$^4$)—CH$_2$— or —CH$_2$—N(R$^4$)—;

R$^1$ is lower alkyl, lower alkenyl, cycloalkyl, or is aryl, optionally substituted by one or two substituents selected from the group consisting of halogen, cyano, lower alkyl, CF₃, OCF₃ and lower alkoxy, or is heteroaryl, optionally substituted by one or two substituents selected from the group consisting of halogen, lower alkyl, CF₃ and lower alkoxy;

R² is lower alkyl, cycloalkyl, or is aryl, optionally substituted by one or two substituents selected from the group consisting of halogen, lower alkyl, CF₃, and lower alkoxy, or is heteroaryl, optionally substituted by one or two substituents selected from the group consisting of halogen, lower alkyl, CF₃ and lower alkoxy;

R³ is hydrogen, lower alkyl or benzyl;
R⁴ is hydrogen or benzyl; and
n is 0, 1 or 2;

or a pharmaceutically acceptable salt thereof.

Especially preferred are those compounds of formula I,

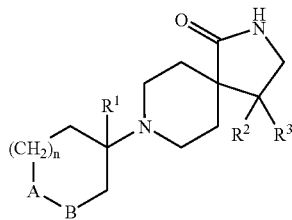

I wherein
A-B is —CH₂—CH₂—, —CH₂—O—, —O—CH₂—, —S—CH₂— or —N(R⁴)—CH₂—;

R¹ is lower alkyl, lower alkenyl, cycloalkyl, or is phenyl, optionally substituted by one or two substituents selected from the group consisting of halogen, cyano, lower alkyl, CF₃, OCF₃ and lower alkoxy, or is heteroaryl, optionally substituted by lower alkyl;

R² is lower alkyl, or is phenyl, optionally substituted by one substituent selected from the group consisting of halogen, lower alkyl, CF₃, and lower alkoxy, or is heteroaryl;

R³ is hydrogen;
R⁴ is benzyl; and
n is 1 or 2;

or a pharmaceutically acceptable salt thereof.

Further are compounds, wherein n is 1, for example, compounds where —A-B— is —CH₂—CH₂— and n is 1.

Especially preferred from this group are compounds, wherein R¹ is phenyl, optionally substituted by halogen or lower alkyl. Within this group of compounds, those in which R² is phenyl are preferred, for example the following compounds rac-4-Phenyl-8-(1-phenyl-cyclohexyl)-2,8-diaza-spiro[4.5]decan-1-one;
rac-4-Phenyl-8-(1-p-tolyl-cyclohexyl)-2,8-diaza-spiro[4.5]decan-1-one;
rac-4-Phenyl-8-(1-m-tolyl-cyclohexyl)-2,8-diaza-spiro[4.5]decan-1-one;
rac-4-Phenyl-8-(1-o-tolyl-cyclohexyl)-2,8-diaza-spiro[4.5]decan-1-one;
rac-8-[1-(3-Fluoro-phenyl)-cyclohexyl]-4-phenyl-2,8-diaza-spiro[4.5]decan-1-one;
rac-8-[1-(3,4-Difluoro-phenyl)-cyclohexyl]-4-phenyl-2,8-diaza-spiro[4.5]decan-1-one;
rac-8-[1-(4-Chloro-phenyl)-cyclohexyl]-4-phenyl-2,8-diaza-spiro[4.5]decan-1-one; and
rac-4-Phenyl-8-[1-(4-trifluoromethyl-phenyl)-cyclohexyl]-2,8-diaza-spiro[4.5]decan-1-one.

Also preferred within this group are compounds in which R² is phenyl substituted by halogen or alkyl, for example, the following compounds rac-4-(4-Fluoro-phenyl)-8-(1-p-tolyl-cyclohexyl)-2,8-diaza-spiro[4.5]decan-1-one;
rac-4-(4-Fluoro-phenyl)-8-(1-m-tolyl-cyclohexyl)-2,8-diaza-spiro[4.5]decan-1-one;
rac-4-(4-Fluoro-phenyl)-8-(1-o-tolyl-cyclohexyl)-2,8-diaza-spiro[4.5]decan-1-one;
rac-4-(4-Fluoro-phenyl)-8-[1-(4-fluoro-phenyl)-cyclohexyl]-2,8-diaza-spiro[4.5]decan-1-one;
rac-4-(4-Fluoro-phenyl)-8-[1-(3-fluoro-phenyl)-cyclohexyl]-2,8-diaza-spiro[4.5]decan-1-one;
rac-8-[1-(3,4-Difluoro-phenyl)-cyclohexyl]-4-(4-fluoro-phenyl)-2,8-diaza-spiro[4.5]decan-1-one;
rac-8-[1-(4-Chloro-phenyl)-cyclohexyl]-4-(4-fluoro-phenyl)-2,8-diaza-spiro[4.5]decan-1-one;
rac-4-(4-Fluoro-phenyl)-8-[1-(4-trifluoromethyl-phenyl)-cyclohexyl]-2,8-diaza-spiro[4.5]decan-1-one;
rac 8-(1-Phenyl-cyclohexyl)-4-p-tolyl-2,8-diaza-spiro[4.5]decan-1-one;
rac 8-[1-(4-Fluoro-phenyl)-cyclohexyl]-4-p-tolyl-2,8-diaza-spiro[4.5]decan-1-one; and
rac 8-[1-(4-Fluoro-phenyl)-cyclohexyl]-4-(4-trifluoromethyl-phenyl)-2,8-diaza-spiro[4.5]decan-1-one.

Further preferred compounds within this group are those in which R² is phenyl substituted by alkoxy, for example, rac 8-[1-(4-Fluoro-phenyl)-cyclohexyl]-4-(4-methoxy-phenyl)-2,8-diaza-spiro[4.5]decan-1-one.

Another group of preferred compounds in which —A-B— is —CH₂—CH₂— and n is 1 are those in which R¹ is thiophenyl and R² is phenyl substituted by halogen. Examples of such compounds are rac-4-Phenyl-8-(1-thiophen-3-yl-cyclohexyl)-2,8-diaza-spiro[4.5]decan-1-one;
rac-4-(4-Fluoro-phenyl)-8-(1-thiophen-2-yl-cyclohexyl)-2,8-diaza-spiro[4.5]decan-1-one;
rac-4-(4-Fluoro-phenyl)-8-[1-(5-methyl-thiophen-2-yl)-cyclohexyl]-2,8-diaza-spiro[4.5]decan-1-one; and
rac-4-(4-Fluoro-phenyl)-8-(1-thiophen-3-yl-cyclohexyl)-2,8-diaza-spiro[4.5]decan-1-one.

Another preferred group of compounds are compounds in which R² is lower alkyl. Within this group, preferred compounds are those wherein R¹ is phenyl, for example, the following compounds rac 8-(1-Phenyl-cyclohexyl)-4-propyl-2,8-diaza-spiro[4.5]decan-1-one and
rac 8-[1-(4-Fluoro-phenyl)-cyclohexyl]-4-propyl-2,8-diaza-spiro[4.5]decan-1-one.

Also preferred within this group, are compounds wherein R¹ is thiophenyl optionally substituted by alkyl, for example the following compounds rac 4-Propyl-8-(1-thiophen-2-yl-cyclohexyl)-2,8-diaza-spiro[4.5]decan-1-one and
rac 8-[1-(5-Methyl-thiophen-2-yl)-cyclohexyl]-4-propyl-2,8-diaza-spiro[4.5]decan-1-one.

Another preferred group of compounds in which —A-B— is —CH₂—CH₂— and n is 1 are those in which R¹ is phenyl substituted by cyano. Examples of such compounds include rac-4-[1-(1-Oxo-4-phenyl-2,8-diaza-spiro[4.5]dec-8-yl)-cyclohexyl]-benzonitrile;
rac-3-[1-(1-Oxo-4-phenyl-2,8-diaza-spiro[4.5]dec-8-yl)-cyclohexyl]-benzonitrile;

rac-4-{1-[4-(4-Fluoro-phenyl)-1-oxo-2,8-diaza-spiro[4.5] dec-8-yl]-cyclohexyl}-benzonitrile; and
rac-3-{1-[4-(4-Fluoro-phenyl)-1-oxo-2,8-diaza-spiro[4.5] dec-8-yl]-cyclohexyl}-benzonitrile.

A further preferred group of such compounds are those in which $R^1$ is phenyl substituted by lower alkoxy or $OCF_3$, for example, the following compounds
rac-8-[1-(4-Methoxy-phenyl)-cyclohexyl]-4-phenyl-2,8-diaza-spiro[4.5]decan-1-one;
rac-8-[1-(3-Methoxy-phenyl)-cyclohexyl]-4-phenyi-2,8-diaza-spiro[4.5]decan-1-one;
rac-8-[1-(2-Methoxy-phenyl)-cyclohexyl]-4-phenyl-2,8-diaza-spiro[4.5]decan-1-one;
rac-4-Phenyl-8-[1-(4-trifluoromethoxy-phenyl)-cyclohexyl]-2,8-diaza-spiro[4.5]decan-1-one;
rac-4-Phenyl-8-[1-(3-trifluoromethoxy-phenyl)-cyclohexyl]-2,8-diaza-spiro[4.5]decan-1-one;
rac-4-(4-Fluoro-phenyl)-8-[1-(4-methoxy-phenyl)-cyclohexyl]-2,8-diaza-spiro[4.5]decan-1-one;
rac-4-(4-Fluoro-phenyl)-8-[1-(3-methoxy-phenyl)-cyclohexyl]-2,8-diaza-spiro[4.5]decan-1-one;
rac-4-(4-Fluoro-phenyl)-8-[1-(4-trifluoromethoxy-phenyl)-cyclohexyl]-2,8-diaza-spiro[4.5]decan-1-one; and
rac-4-(4-Fluoro-phenyl)-8-[1-(3-trifluoromethoxy-phenyl)-cyclohexyl]-2,8-diaza-spiro[4.5]decan-1-one.

Another preferred group of compounds in which —A-B— is —$CH_2$—$CH_2$— and n is 1 are those in which $R^1$ is lower alkyl or lower alkenyl, for example, the following compounds
rac-8-(1-Isopropyl-cyclohexyl)-4-phenyl-2,8-diaza-spiro[4.5]decan-1-one;
rac 8-[1-(2-Methyl-propenyl)-cyclohexyl]-4-phenyl-2,8-diaza-spiro[4.5]decan-1-one;
rac-8-(1-Cyclopropyl-cyclohexyl)-4-(4-fluoro-phenyl)-2,8-diaza-spiro[4.5]decan-1-one; and
rac-8-(1-Ethyl-cyclohexyl)-4-(4-fluoro-phenyl)-2,8-diaza-spiro[4.5]decan-1-one.

A further preferred group of compounds are those in which $R^1$ is cycloalkyl, for example, the compounds
rac-8-Bicyclohexyl-1-yl-4-phenyl-2,8-diaza-spiro[4.5]decan-1-one;
rac-8-(1-Cyclopentyl-cyclohexyl)-4-phenyl-2,8-diaza-spiro[4.5]decan-1-one;
rac-8-(1-Cyclopropyl-cyclohexyl)-4-phenyl-2,8-diaza-spiro[4.5]decan-1-one; and
rac-8-(1-Cyclopropyl-cyclohexyl)-4-(4-fluoro-phenyl)-2,8-diaza-spiro[4.5]decan-1-one.

Also preferred are such compounds wherein $R^1$ is thiophenyl optionally substituted by lower alkyl, for example,
rac 8-(1-Phenyl-cyclohexyl)-4-thiophen-2-yl-2,8-diaza-spiro[4.5]decan-1-one.

Other preferred compounds in which A-B is —$CH_2$—$CH_2$— and n is 1 are those in which $R^1$ is heteroaryl optional substituted by lower alkyl, for example
rac-4-(4-Fluoro-phenyl)-8-(1-thiazol-2-yl-cyclohexyl)-2,8-diaza-spiro[4.5]decan-1-one.

Further preferred are compounds of the invention, wherein —A-B— is —O—$CH_2$—, —$CH_2$O—, —S—$CH_2$— or —N(benzyl)—$CH_2$— and n is 1. For example, compounds of the invention in which —A-B—is —O—$CH_2$—, such as rac-4-Phenyl-8-(4-phenyl-tetrahydro-pyran-4-yl)-2,8-diaza-spiro[4.5]decan-1-one are preferred.

Also, compounds in which —A-B— is —$CH_2$O—, such as 4-Phenyl-8-(3-phenyl-tetrahydro-pyran-3-yl)-2,8-diaza-spiro[4.5]decan-1-one are preferred.

Also preferred are those compounds in which —A-B— is —S—$CH_2$—, for example the following compounds
rac-4-(4-Fluoro-phenyl)-8-(4-phenyl-tetrahydro-thiopyran-4-yl)-2,8-diaza-spiro[4.5]decan-1-one and
rac-4-(4-Fluoro-phenyl)-8-[4-(4-fluoro-phenyl)-tetrahydro-thiopyran-4-yl]-2,8-diaza-spiro[4.5]decan-1-one.

Further preferred are compounds in which —A-B— is —N(benzyl)—$CH_2$—, such as
rac-8-[1-Benzyl-4-(4-fluoro-phenyl)-piperidin-4-yl]-4-(4-fluoro-phenyl)-2,8-diaza-spiro[4.5]decan-1-one.

A further object of the present invention are compounds of formula I, wherein n is 2. Examples from this group are the following compounds
rac-4-Phenyl-8-(1-phenyl-cycloheptyl)-2,8-diaza-spiro[4.5]decan-1-one;
rac-4-(4-Fluoro-phenyl)-8-(1-phenyl-cycloheptyl)-2,8-diaza-spiro[4.5]decan-1-one; and
rac-4-(4-fluoro-phenyl)-8-[1-(4-fluoro-phenyl)-cycloheptyl]-2,8-diaza-spiro[4.5]decan-1-one.

The present compounds of formula I and their pharmaceutically acceptable salts can be prepared by methods known in the art, for example, by processes described below, which process comprises a) reacting a compound of formula

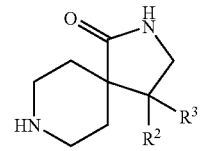

6 with a compound of formula

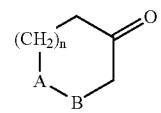

7 in the presence of AcOH and TMSCN and then with a corresponding Grignard reagent of formula $R^1MgHal$ 9 to produce a compound of formula

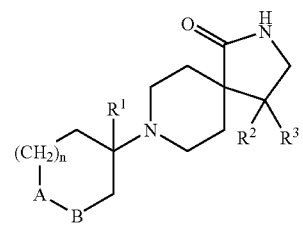

I wherein the substituents are as described above and hal is Cl, Br or I, and b) if desired, separating the obtained racemic forms into corresponding enantiomers, and if desired, converting the compounds obtained into pharmaceutically acceptable salts.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I may be prepared in accordance with process variants a) and b) and with the following schemes 1 and 2.

The starting materials of formulas 1, 2 and 7 are commercially available or may beprepared in accordance with known methods.

The following abbreviations have been used:
LDA=lithiumdiisopropylamide
TMSCN=trimethylthiocyanat
DCM=dichloromethane
TFA=trifluoroacetic acid
THF=tetrahydrofuran Starting from an appropriately 1-protected-piperidine-4-ethylcarboxylate 1, treatment with an appropriate base, usually LDA, followed by treatment with an appropriately substituted nitro alkene 2 results in formation of the nitro alkane 3. Reduction to the amino group facilitated by Raney-Ni and hydrogen, usually at 60 bar pressure and at 55° C. in EtOH as solvent results in the formation of 4. Subsequent cyclisation by heating in toluene under reflux affords the amide 5. Removal of the protecting group under standard conditions (TFA treatment in DCM for R=Boc; or hydrogenolysis with Pd/C in DCM, MeOH for R=Bn) affords the diazaspiropiperidines 6 (Scheme 1).

Scheme 1

Step 1

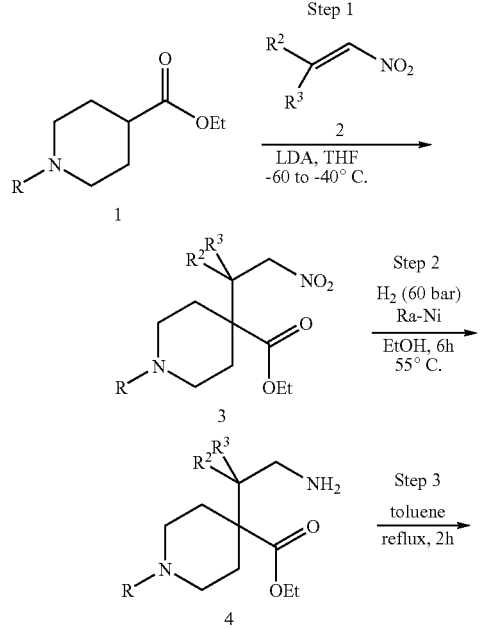

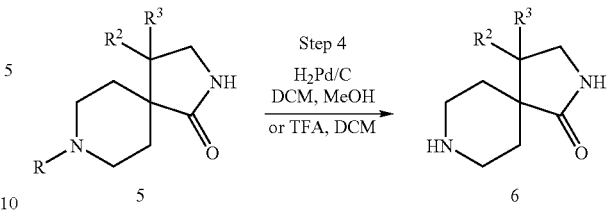

wherein R is an N-protecting group, such as BOC or benzyl, and the other substituents are as described above.

Compounds of formula 6 are treated, under Strecker reaction conditions, with a compound of formula 7 in the presence of AcOH and a cyanide source (preferably TMSCN) to give a compound of formula 8, which are then treated, under Bruylant reaction conditions, with a corresponding Grignard reagent 9 to give compounds of formula 1 (Scheme 2). Strecker synthesis can also be carried out using suitable cyanating reagents (KCN, acetonecyanohydrin) according to known procedures at temperature ranges from 0 to 100° C. with reaction times between 30 min and 7 days. Bruylant reactions can be carried out using Grignard reagents prepared from Mg(O) or from i-PrMgCl or other known reagents in a suitable solvent such as tetrahydrofuran (THF). Suitable Grignard reagents are represented by formula $R^1$-Mghal 9.

Scheme 2

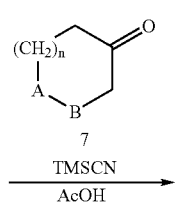

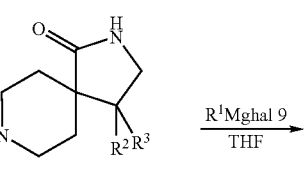

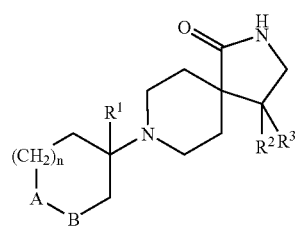

hal = Cl, Br, I

All compounds of formulas I, 3, 4, 5, 6 and 8 can be prepared in racemic form following the procedures described below and separated into chiral non-racemic enantiomers by preparative HPLC using either a Chiralpak OD or AD column (5×50 cm) at room temperature using an ethanol:heptane mobile phase with UV detection at 220 nM.

The compounds of formula I and their pharmaceutically usable addition salts possess valuable pharmacological properties. Specifically, it has been found that the compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycinl % (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat no. R758-07)cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 □M non-radioactive glycine. The plates were incubated with gentle shaking and the reaction was stopped by aspiration of the mixture and washing (three times) with ice-cold US. The cells were lysed with scintillation liquid, shaken 3 hours and the radioactivity in the cells was coounted using a scintillation counter.

Examples of GlyT-1 inhibition can be shown in mouse and human:

| Example No. | GlyT-1 Racemat Mouse/human (nMol) | GlyT-1 Enant. Mouse/human (nMol) |
|---|---|---|
| 1 | 115/118 | 115, 160/77, 107 |
| 25 | 103/95 | 56, 73/nd, 97 |
| 36 | 67/— | 75, nd/281, 381 |
| 38 | 99/— | 99, 213/— |
| 50 | —/132 | 81, 153/— |
| 52 | —/73 | |
| 56 | —/161 | —/62, 82 |
| 57 | —/93 | |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragees, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semiliquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The present invention also provides methods of using the compounds of the invention. For example, the invention provides a method of treating schizophrenia which comprises administering to an individual a therapeutically effective amount of a compound of the invention, for example a compound of formula I or a pharmaceutically acceptable salt thereof. The invention also provides a method of treating Alzheimer's disease which comprises administering to an individual a therapeutically effective amount of a compound of the invention, for example a compound of formula I or a pharmaceutically acceptable salt thereof. The present invention further provides a method of reducing pain which comprises administering to an individual a therapeutically effective amount of a compound of the invention, for example a compound of formula I or a pharmaceutically acceptable salt thereof. The invention also provides a method of improving cognition which comprises administering to an individual a therapeutically effective amount of a compound of the invention, for example a compound of formula I or a pharmaceutically acceptable salt thereof.

The most preferred indications in accordance with the present invention are those, which include disorders of the central nervous system, for example the treatment or prevention of schizophrenia, cognitive impairment and Alzheimer's disease.

The compounds and compositions of the present invention can be administered in a conventional manner, for example, orally, rectally, or parenterally. The pharmaceutical compositions of the invention can be administered orally, for example, in the form of tablets, coated tablets, dragees, hard and soft gelatine capsules, solutions, emulsions or suspensions. The pharmaceutical compositions also can be administered rectally, for example, in the form of suppositories or parenterally, for example, in the form of injection solutions.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it. All temperatures are given in degree Celsius.

Preparation of Building Blocks 6
rac-4-Phenyl-2,8-diaza-spiro[4.5]decan-1-one rac-1-Benzyl-4-(2-nitro-1-phenyl-ethyl-piperidine-4-carboxylic acid ethyl ester a) An LDA (14 mmol) solution was prepared by treating diisopropylamine (1.37 g, 14 mmol) with BuLi (1.6 M, 8.5 mL, 14 mmol) at −78° C. in dry THF (10 mL) under Argon and allowing to warm up to −20° C. This solution was then cooled to −60° C. added to a solution of 1-benzyl-piperidine-4-ethyl carboxylate (3.05 g, 12 ramol) at −60° C. and allowed to warm up to −40° C. over 1 h whereupon a solution of trans-beta-nitrostyrene (1.93 g, 13 mmol) was added dropwise. The reaction mixture was allowed to warm up to room temperature over 1 h and then quenched with ammonium chloride (saturated, 40 mL) and the product extracted with ethyl acetate (2×40 mL). The combined organic extracts were then washed with brine, dried over sodium sulfate, filtered and evaporated. Purification by chromatography on silica gel eluting with DCM: MeOH (9:1) afforded the title compound (4.1 g, 84%) as a light yellow gum. MS: m/e=397.4 (M+H).

rac-4-(2-Amino-1-phenyl-ethyl)-1-benzyl-piperidine-4-carboxylic acid ethyl ester b) A solution of rac-1-benzyl-4-(2-nitro-1-phenyl-ethyl)-piperidine-4-carboxylic acid ethyl ester (3.18 g, 8 mmol) in dry EtOH (240 mL) was hydrogenated in the presence of Ra—Ni (3 g) at 60 bar at 55° C. for 3 h. After cooling and decompression of the reaction vessel, the mixture was filtered over celite and the filtrate evaporated to leave the title compound (2.9 g, 99%) as a clear oil. MS: m/e=367.4 (M+H).

rac-8-Benzyl-4-phenyl-2 8-diaza-spiro[4.5]decan-1-one c) A solution of rac-4-(2-amino-1-phenyl-ethyl)-1-benzyl-piperidine-4-carboxylic acid ethyl ester (2.9 g, 8 mmol) in toluene (30 mL) was heated under reflux for 4 h. After cooling to room temperature and evaporation the mixture was purified by chromatography on silica gel eluting with DCM:MeOH:NH$_4$OH (95:4.5:0.5) to afford the title compound (1.47 g, 58%) as a white solid. MS: m/e=321.4 (M+H).

rac-4-Phenyl-2,8-diaza-spiro[4.5]decan-1-one d) A suspension of rac-8-benzyl-4-phenyl-2,8-diaza-spiro[4.5]decan-1-one (28.8 g, 90 mmol) in MeOH: DCM (4: 1, 500 ml) was hydrogenated in the presence of Pd (10% on C, 14 g, 132 mmol) at 2 bar for 48 h at room temperature. After filtration over celite, the reaction mixture was evaporated and the residue dissolved in NaOH (2 N, 200 mnL). The product was extracted with DCM (3×150 mL) and the combined organic extracts dried over sodium sulfate. Filtration and evaporation afforded the title compound (13.1 g, 63%) as a white solid after trituration from diethylether. MS: m/e=231.4 (M+H).

Scheme 1, Step 1: F-derivative from Boc protecting group rac-4-(4-Fluoro-phenyl)-2,8-diaza-spiro [4.5]decan-1-one Piperidine-1,4-dicarboxylic acid 1-tert-butyl ester 4-ethyl ester a) To a solution of ethyl isonipecotate (20 g, 127 mmol) in dioxane:water (1:1, 120 mlL) was added triethylamine (12.87 g, 127 mmol) at 0° C. followed by di-tert-butylcarbonate (35.2 g, 161 mmol) and the resulting mixture maintained at this temperature for 2 h. The product was then extracted with ethyl acetate (3×100 mL) and the combined organic extracts washed with HCl (1 N, 100 mL), brine (100 miL), dried over sodium sulfate, filtered and evaporated. Purification by Kugelrohr distillation afforded the title compound (29.0 g, 89%) as a colourless liquid, bp 140° C. at 0.13 mbar. MS: m/e=275.2 (M+NH$_4$).

rac-4-[1-(4-Fluoro-phenyl)-2-nitro-ethyl]-piperidine-11 44-dicarboxylic acid 1-tert-butyl ester 4-ethyl ester b) An LDA solution was prepared by treating diisopropylamine (6.98 g, 69 mmol) with BuLi (1.6 M, 41.3 mL, 66 mmol) at −78° C. in dry THF (45 mL) under Argon and allowing to warm up to −20° C. This solution was then cooled to −60° C. added to a solution of piperidine-1,4-dicarboxylic acid 1-tert-butyl ester 4-ethyl ester (15.44 g, 60 mmol) in dry THF (45 mL) at −60° C. and allowed to warm up to −40° C. over 1 h whereupon a solution of 4-fluoro-trans-beta-nitrostyrene (10.02 g, 60 mmol) in dry THF (40 mL) was added dropwise. The reaction mixture was allowed to warm up to room temperature over 1 h and then quenched with ammonium chloride (saturated, 250 mL) and the product extracted with diethylether (3×100 mL). The combined organic extracts were then washed with brine, dried over sodium sulfate, filtered and evaporated to afford the title compound (26.7 g, 99%) as a light yellow gum. MS: m/e=442.4 (M+NH$_4$).

rac-4-(2-Amino-1-phenyl-ethyl)-1-tert-butyl-piperidine-14-dicarboxylic acid ethyl ester c) A solution of rac-4-[1-(4-fluoro-phenyl)-2-nitro-ethyl]-piperidine-1,4-dicarboxylic acid 1-tert-butyl ester 4-ethyl ester (26.6 g, 60 mmol) in dry EtOH (600 mL) was hydrogenated in the presence of Ra—Ni (25 g) at 50 bar at 50° C. for 20 h. After cooling and decompression of the reaction vessel, the mixture was filtered over celite and the filtrate evaporated to leave the title compound (23.4 g, 99%) as a clear oil which was used directly in the next step.

rac-4-(4-Fluoro-phenyl)-1-oxo-2 8-diaza-spiro[4.5]decane-8-carboxylic acid tert-butyl ester d) A solution of rac-4-(2-arnino-1-phenyl-ethyl)-1-tert-butyl-piperidine-1,4-dicarboxylic acid ethyl ester (23.4 g, 60 mmol) in toluene (200 mL) was heated under reflux for 18 h. After cooling to room temperature, evaporation afforded the title compound (17.17 g, 83%) as a white solid after trituration from hot pentane. MS: m/e=349.3 (M+H).

rac-4-(4-Fluoro-phenyl)-2 8-diaza-spiro[4.5]decan-1-one e) A solution of rac-4-(4-fluoro-phenyl)-1-oxo-2,8-diaza-spiro[4.5]decane-8-carboxylic acid tert-butyl ester (46.0 g, 132 mmol) in DCM (260 mL) containing TFA (150 mL, 1.32 mol) was stirred vigorously at 0° C. for 15 min. The reaction mixture was then poured into NaOH (3 N, 200 mL) and the product extracted with DCM (3×100 mL). The combined organic extracts were then washed with water (100 mL) and brine (100 mL) and then dried over sodium sulfate. Filtration and evaporation afforded the title compound (22.14 g, 68%) as a white solid after trituration from ethyl acetate. MS: m/e=249.2 (M+H).

(R)-4-(4-Fluoro-phenyl)-2,8-diaza-spiro[4.5]decan-1-one and (S)-4-(4-Fluoro-phenyl)-2,8-diaza-spiro [4.5]decan-1-one The enantiomers of rac-4-(4-fluoro-phenyl)-2,8-diaza-spiro[4.5]decan-1-one were separated using a 5×50 cm Chiralpak AD column at room temperature using a 15% ethanol: 85% heptane mobile phase with UV detection at 220 riM. Less polar component (Peak 1) corresponds to the (R)-enantiomer (see below).

Elucidation of absolute stereochemistry: To a solution of 4-(4-fluoro-phenyl)-2,8-diaza-spiro[4.5]decan-1-one (Peak A, 50 mg, 0.2 mmol) in methanol (10 mL) was added 1R-(−)-camphorsulfonic acid (46.8 mg, 0.2 mmol) and the solution stirred for 10 min at room temperature. The resulting mixture was evaporated and the residue crystallized from ethyl acetate. A single crystal X-ray structural analysis determined the absolute configuration was (R)- as 1R-(−)-camphorsulfonic acid salt.

Preparation of Building blocks 8 rac-1-(1-Oxo-4-phenyl-2,8-diaza-spiro [4.5]dec-8-yl)-cyclohexanecarbonitrile To a mixture of rac-4-phenyl-2,8-diaza-spiro[4.5]decan-1-one (8.0 g, 34.7 mmol) in AcOH (80 mL) was added cyclohexanone (3-4 g, 34.7 mmol) followed by the dropwise addition of TMSCN (10.4 g, 104.2 mmol) and the resulting mixture stirred at room temperature for 5 days. The resulting mixture was poured onto ice—sodium hydroxide (25%, 200 mL) and the resulting white solid filtered off. The solid was dissolved in DCM (50 mL) and washed with water (40 mL) and dried over sodium sulfate. Filtration and evaporation afforded the title compound (7.25 g, 62%) as a white solid after purification by silica gel chromatography eluting with DCM: MeOH (9: 1). MS: m/e=338.3 (M+H).

rac-1-[4-(4-Fluoro-phenyl)-1-oxo-2,8-diaza-spiro [4.5]dec-8-yl]-cyclohexanecarbonitrile As described above, rac-4-(4-fluoro-phenyl)-2,8-diaza-spiro[4.5]decan-1-one (10.0 g, 40.3 mmol) was converted to the title compound (8.0 g, 56%) which was obtained as a white solid. MS: m/e=356.5 (M+H).

(R)-1-[4-(4-Fluoro-phenyl)-1-oxo-2,8-diaza-spiro [4.5]dec-8-yl]-cyclohexanecarbonitrile As described above, (R)-4-(4-fluoro-phenyl)-2,8-diaza-spiro[4.5]decan-1-one (Peak A, 150 mg, 0.4 mmol) was converted to the title compound (116 mg, 54%) which was obtained as a white solid. MS: m/e=356.5 (M+H).

(S)-1-[4-(4-Fluoro-phenyl)-1-oxo-2,8-diaza-spiro [4.5]dec-8-yl]-cyclohexanecarbonitrile As described above, (S)-4-(4-fluoro-phenyl)-2,8-diaza-spiro[4.5]decan-1-one (Peak B, 150 mg, 0.4 mmol) was converted to the title compound (116 mg, 54%) which was obtained as a white solid. MS: m/e=356.5 (M+H).

EXAMPLE 1 rac-4-Phenyl-8-(1-phenyl-cyclohexyl)-2,8-diaza-spiro[4.5]decan-1-one

To a solution of rac-1-(1-oxo-4-phenyl-2,8-diaza-spiro [4.5]dec-8-yl)-cyclohexanecarbonitrile (400 mg, 1.2 mmol) in dry THF (12 mL) under argon at 0° C. was added phenylmagnesium bromide (1 M in THF, 3.5 mL, 3.6 mmol) and the resulting mixture allowed to warm up to room temperature overnight. The reaction was quenched by the addition of ammonium chloride solution (sat., 20 mL) and the product extracted with ethyl acetate (2×50 mL). The combined organic extracts were then washed with brine (50 mL), dried over sodium sulfate, filtered and evaporated. The residue was purified by chromatography on silica gel eluting with DCM:MeOH:NH$_4$OH (95:4.5:0.5) to afford the title compound (430 mg, 94%) as a white solid. MS: m/e=389.3 (M+H).

EXAMPLE 2 rac4-Phenyl-8-(1-p-tolyl-cyclohexyl)-2,8-diaza-spiro [4.5]decan-1-one

As described for example 1, rac-1-(1-oxo-4-phenyl-2,8-diaza-spiro[4.5]dec-8-yl)-cyclohexanecarbonitrile (200 mg, 0.6 mmol) was converted to the title compound (186 mg, 78%) (using p-tolylmagnesium bromide instead of phenylmagnesium bromide) which was obtained as a white solid. MS: m/e=403.6 (M+H).

EXAMPLE 3 rac-4-Phenyl-8-(1-m-tolyl-cyclohexyl)-2,8-diaza-spiro[4.5]decan-1-one

To a solution of 3-iodotoluene (388 mg, 1.8 mmol) in dry THF (6 mL) under argon at -60° C. was added isopropylmagnesium chloride (2 M solution in THF, 977 μL, 2.0 mmol) and the resulting solution allowed to warm up to 0° C. over 1 h and then to room temperature over 10 min. The resulting solution was then added dropwise to a solution of rac-1-(1-oxo-4-phenyl-2,8-diaza-spiro[4.5]dec-8-yl)-cyclohexanecarbonitrile (200 mg, 0.6 mmol) in dry THF (3 mL) and the solution stirred overnight at room temperature. The reaction was quenched by the addition of ammonium chloride solution (sat., 10 mL) and the product extracted with ethyl acetate (2×20 mL). The combined organic extracts were then washed with brine (20 mL), dried over sodium sulfate, filtered and evaporated. The residue was purified by

EXAMPLE 4 rac4-Phenyl-8-(1-o-tolyl-cyclohexyl)-2,8-diaza-spiro[4.5]decan-1-one

As described for example 3, rac-1-(1-oxo-4-phenyl-2,8-diaza-spiro[4.5]dec-8-yl)-cyclohexanecarbonitrile (200 mg, 0.6 mmol) was converted to the title compound (11 mg, 5%) (using 2-iodotoluene instead of 3-iodotoluene) which was obtained as a white solid. MS: m/e=403.6 (M+H).

EXAMPLE 5 rac-8-[1-(3-Fluoro-phenyl)-cyclohexyl]4-phenyl-2,8-diaza-spiro[4.5]decan-1-one

As described for example 3, rac-1-(1-oxo-4-phenyl-2,8-diaza-spiro[4.5]dec-8-yl)-cyclohexanecarbonitrile (200 mg, 0.6 mmol) was converted to the title compound (146 mg, 61%) (using 1-fluoro-3-iodobenzene instead of 3-iodotoluene) which was obtained as a white solid. MS: m/e=407.5 (M+H).

EXAMPLE 6 rac-8-[1-(3,4-Difluoro-phenyl)-cyclohexyl]-4-phenyl-2,8-diaza-spiro[4.5]decan-1-one As described for example 3, rac-1-(1-oxo-4-phenyl-2,8-diaza-spiro[4.5]dec-8-yl)-cyclohexanecarbonitrile (200 mg, 0.6 mmol) was converted to the title compound (96 mg, 38%) (using 1,2-difluoro-4-iodobenzene instead of 3-iodotoluene) which was obtained as a white solid. MS: m/e=425.6 (M+H).

EXAMPLE 7 rac-8-[1-(4-Chloro-phenyl)-cyclohexyl]-4-phenyl-2,8-diaza-spiro[4.5]decan-1-one

As described for example 3, rac-1-(1-oxo-4-phenyl-2,8-diaza-spiro[4.5]dec-8-yl)-cyclohexanecarbonitrile (200 mg, 0.6 mmol) was converted to the title compound (96 mg, 38%) (using 1-chloro-4-iodobenzene instead of 3-iodotoluene) which was obtained as a white solid. MS: m/e=423.4 (M).

EXAMPLE 8 rac4-Phenyl-8-[d-(4-trifluoromethyl-phenyl)-cyclohexyl]-2,8-diaza-spiro[4.5]decan-1-one As described for example 3, rac-1-(1-oxo-4-phenyl-2,8-diaza-spiro[4.5]dec-8-yl)-cyclohexanecarbonitrile (200 mg, 0.6 mmol) was converted to the title compound (169 mg, 63%) (using 4-iodobenzotrifluoride instead of 3-iodotoluene) which was obtained as a white solid. MS: m/e=457.6 (M+H).

EXAMPLE 9 rac4-[1-(1-Oxo4-phenyl-2,8-diaza-spiro [4.5]dec-8-yl)-cyclohexyl]-benzonitrile

As described for example 3, rac-1-(1-oxo-4-phenyl-2,8-diaza-spiro[4.5]dec-8-yl)-cyclohexanecarbonitrile (200 mg, 0.6 mmol) was converted to the title compound (81 mg, 33%) (using 4-iodobenzonitrile instead of 3-iodotoluene) which was obtained as a white solid. MS: m/e=414.5 (N+H).

EXAMPLE 10 rac-3-[1-(1-Oxo4-phenyl-2,8-diaza-spiro[4.5]dec-8-yl)-cyclohexyl]-benzonitrile

As described for example 3, rac-1-(1-oxo-4-phenyl-2,8-diaza-spiro[4.5]dec-8-yl)-cyclohexanecarbonitrile (200 mg, 0.6 mmol) was converted to the title compound (77 mg, 31%) (using 3-iodobenzonitrile instead of 3-iodotoluene) which was obtained as a white solid. MS: m/e=414.5 (M+H).

EXAMPLE 11 rac-8-[1-(4-Methoxy-phenyl)-cyclohexyl]-4-phenyl-2,8-diaza-spiro[4.5]decan-1-one As described for example 1, rac-1-(1-oxo-4-phenyl-2,8-diaza-spiro[4.5]dec-8-yl)-cyclohexanecarbonitrile (200 mg, 0.6 mmol) was converted to the title compound (68 mg, 27%) (using 4-methoxyphenylmagnesium bromide instead of phenylmagnesium bromide) which was obtained as a white solid. MS: m/e=437.5 (M+H).

EXAMPLE 12 rac-8-[1-(3-Methoxy-phenyl)-cyclohexyl]-4-phenyl-2,8-diaza-spiro[4.5]decan-1-one As described for example 3, rac-1-(1-oxo-4-phenyl-2,8-diaza-spiro[4.5]dec-8-yl)-cyclohexanecarbonitrile (200 mg, 0.6 mmol) was converted to the title compound (150 mg, 61%) (using 3-iodoanisole instead of 3-iodotoluene) which was obtained as a white solid. MS: m/e=419.5 (M+H).

EXAMPLE 13 rac-8-[1-(2-Methoxy-phenyl)-cyclohexyl]4-phenyl-2,8-diaza-spiro[4.5]decan-1-one

As described for example 3, rac-1-(1-oxo-4-phenyl-2,8-diaza-spiro[4.5]dec-8-yl)-cyclohexanecarbonitrile (200 mg, 0.6 mmol) was converted to the title compound (37 mg, 15%) (using 2-iodoanisole instead of 3-iodotoluene) which was obtained as a white solid. MS: m/e=419.5 (M+H).

EXAMPLE 14 rac-4-Phenyl-8-[1-(4-triduoromethoxy-phenyl)-cyclohexyl]-2,8-diaza-spiro[4.5]decan-1-one As described for example 3, rac-1-(1-oxo-4-phenyl-2,8-diaza-spiro[4.5]dec-8-yl)-cyclohexanecarbonitrile (200 mg, 0.6 numol) was converted to the title compound (19 mg, 7%) (using 1-bromo-4-(trifluoromethoxy)benzene instead of 3-iodotoluene) which was obtained as a white solid. MS: m/e=473.5 (M+H).

EXAMPLE 15 rac4-Phenyl-8-[1-(3-trifluoromethoxy-phenyl)-cyclohexyl]-2,8-diaza-spiro[4.5]decan-1-one As described for example 3, rac-1-(1-oxo-4-phenyl-2,8-diaza-spiro[4.5]dec-8-yl)-cyclohexanecarbonitrile (200 mg, 0.6 mmol) was converted to the title compound (115 mg, 41%) (using 3-(trifluoromethoxy)iodobenzene instead of 3-iodotoluene) which was obtained as a white solid. MS: m/e=473.5 (M+H).

EXAMPLE 16 rac-4-Phenyl-8-(l-thiophen-3-yl-cyclohexyl)-2,8-diaza-spiro[4.5]decan-1-one

As described for example 3, rac-1-(1-oxo-4-phenyl-2,8-diaza-spiro[4.5]dec-8-yl)-cyclohexanecarbonitrile (300 mg, 0.9 mmol) was converted to the title compound (77 mg, 22%) (using 3-bromothiophene instead of 3-iodotoluene) which was obtained as a brown oil. MS: m/e=395.4 (M+H).

EXAMPLE 17 rac-8-Bicyclohexyl-1-yl-4-phenyl-2,8-diaza-spiro[4.5]decan-1-one

As described for example 1, rac-1-(1-oxo-4-phenyl-2,8-diaza-spiro[4.5]dec-8-yl)-cyclohexanecarbonitrile (160 mg, 0.5 mmol) was converted to the title compound (26 mg, 14%) (using cyclohexylmagnesium chloride instead of phenylmagnesium bromide) which was obtained as a white solid. MS: m/e=395.4 (M+H).

EXAMPLE 18 rac-8-(1-Cyclopentyl-cyclohexyl)4-phenyl-2,8-diaza-spiro[4.5]decan-1-one

As described for example 1, rac-1-(1-oxo-4-phenyl-2,8-diaza-spiro[4.5]dec-8-yl)-cyclohexanecarbonitrile (160 mg, 0.5 mmol) was converted to the title compound (46 mg, 26%) (using cyclopentylmagnesium chloride instead of phenylmagnesium bromide) which was obtained as a white solid. MS: m/e=381.5 (M+H).

EXAMPLE 19 rac-8-(1-Cyclopropyl-cyclohexyl)-4-phenyl-2,8-diaza-spiro[4.5]decan-1-one

As described for example 1, rac-1-(1-oxo-4-phenyl-2,8-diaza-spiro[4.5]dec-8-yl)-cyclohexanecarbonitrile (150 mg, 0.44 mmol) was converted to the title compound (21 mg, 12%) (using cyclopropylmagnesium bromide instead of phenylmagnesium bromide) which was obtained as a white solid. MS: m/e=353.4 (M+H).

EXAMPLE 20 rac-8-(1-Isopropyl-cyclohexyl)-4-phenyl-2,8-diaza-spiro [4.5]decan-1-one

As described for example 14, rac-1-(1-oxo-4-phenyl-2,8-diaza-spiro[4.5]dec-8-yl)-cyclohexanecarbonitrile (200 mg, 0.6 mmol) was converted to the title compound (12 mg, 6%) which was obtained as a white solid. MS: m/e=355.5 (M+H).

EXAMPLE 21 rac 8-[1-(2-Methyl-propenyl)-cyclohexyl]-4-phenyl-2,8-diaza-spiro[4.5]decan-1-one As described for example 1, rac-1-(1-oxo-4-phenyl-2,8-diaza-spiro[4.5]dec-8-yl)-cyclohexanecarbonitrile (160 mg, 0.47 mmol) was converted to the title compound (55 mg, 32%) (using 2-methyl-1-propenylmagnesium bromide instead of phenylmagnesium bromide) which was obtained as a white solid. MS: m/e=367.3 (M+H).

EXAMPLE 22 rac-4-(4-Fluoro-phenyl)-8-(1-p-tolyl-cyclohexyl)-2,8-diaza-spiro[4.5]decan-1-one As described for example 2, rac-4-(4-fluoro-phenyl)-2,8-diaza-spiro[4.5]decan-1-one (200 mg, 0.6 mmol) was converted to the title compound (173 mg, 73%) which was obtained as a white solid. MS: m/e=421.4 (M+H).

EXAMPLE 23 rac-4-(4-Fluoro-phenyl)-8-(1-m-tolyl-cyclohexyl)-2,8-diaza-spiro [4.5]decan-1-one As described for example 3, rac-4-(4-fluoro-phenyl)-2,8-diaza-spiro[4.5]decan-1-one (200 mg, 0.6 mmol) was converted to the title compound (100 mg, 42%) which was obtained as a white solid. MS: m/e=421.5 (M+H).

EXAMPLE 24 rac-4-(4-Fluoro-phenyl)-8-(1-o-tolyl-cyclohexyl)-2,8-diaza-spiro [4.5]decan-1-one As described for example 4, rac-4-(4-fluoro-phenyl)-2,8-diaza-spiro[4.5]decan-1-one (200 mg, 0.6 mmol) was converted to the title compound (36 mg, 15%) which was obtained as a white solid. MS: m/e=421.5 (M+H).

EXAMPLE 25 rac-4-(4-Fluoro-phenyl)-8-[1-(4-fluoro-phenyl)-cyclohexyl]-2,8-diaza-spiro[4.5]decan-1-one As described for example 1, rac-4-(4-fluoro-phenyl)-2,8-diaza-spiro[4.5]decan-1-one (1.0 g, 2.8 mmol) was converted to the title compound (891 mg, 75%) (using 4-fluorophenylmagnesium bromide instead of phenylmagnesium bromide) which was obtained as a white solid. MS: m/e=425.5 (M+H).

(R)-4-(4-Fluoro-phenyl)-8-1-(4-fluoro-phenyl)-cyclohexyll-2,8-diaza-spiro[4.5]decan-1-one As described for example 24-rac, (R)-4-(4-fluoro-phenyl)-2,8-diaza-spiro[4.5]decan-1-one (103 mg, 0.3 mmol) was converted to the title compound (29 mg, 24%)which was obtained as a white solid. MS: m/e=425.5 (M+H).

(S)4-(4-Fluoro-phenyl)-8-[1-(4-fluoro-phenyl)-cyclohexyl]-2,8-diaza-spiro[4.5]decan-1-one As described for example 24-rac, (S)-4-(4-fluoro-phenyl)-2,8-diaza-spiro[4.5]decan-1-one (97 mg, 0.3 miol) was converted to the title compound (35 mg, 30%) which was obtained as a white solid. MS: m/e=425.5 (M+H).

EXAMPLE 26 rac-4-(4-Fluoro-phenyl)-8-[1-(3-fluoro-phenyl)-cyclohexyl]-2,8-diaza-spiro[4.5]decan-1-one As described for example 5, rac-4-(4-fluoro-phenyl)-2,8-diaza-spiro[4.5]decan-1-one (200 mg, 0.6 mmol) was converted to the title compound (180 mg, 75%) which was obtained as a white solid. MS: m/e=425.4 (M+H).

EXAMPLE 27 rac-8-[1-(3,4-Difluoro-phenyl)-cyclohexyl]-4-(4-fluoro-phenyl)2,8-diaza-spiro[4.5]decan-1-one As described for example 6, rac-4-(4-fluoro-phenyl)-2,8-diaza-spiro[4.5]decan-1-one (200 mg, 0.6 mmol) was converted to the title compound (85 mg, 34%) which was obtained as a white solid. MS: m/e=443.5 (M+H).

EXAMPLE 28 rac-8-[1-(4-Chloro-phenyl)-cycloaexyl]-4-(4-fluoro-phenyl)2,8-diaza-spiro[4.5]decan-1-one As described for example 7, rac-4-(4-fluoro-phenyl)-2,8-diaza-spiro[4.5]decan-1-one (200 mg, 0.6 mmol) was converted to the title compound (12 mg, 5%) which was obtained as a white solid. MS: m/e=441.5 (M).

EXAMPLE 29 rac-4-(4-Fluoro-phenyl)-8-[1-(4-trifluoromethyl-phenyl)-cyclohexyl]-2,8-diaza-spiro[4.5]decan-1-one As described for example 8, rac-4-(4-fluoro-phenyl)-2,8-diaza-spiro[4.5]decan-1-one (200 mg, 0.6 mmol) was converted to the title compound (114 mg, 42%) which was obtained as a white solid. MS: m/e=475.6 (M+H).

EXAMPLE 30 rac4-{1-[4-(4-Fluoro-phenyl)-1-oxo-2,8-diaza-spiro[4.5]dec-8-yl]-cyclohexyl}-benzonitrile As described for example 9, rac-4-(4-fluoro-phenyl)-2,8-diaza-spiro[4.5]decan-1-one (200 mg, 0.6 mmol) was converted to the title compound (88 mg, 36%) which was obtained as a white solid. MS: m/e=432.6 (M+H).

EXAMPLE 31 rac-3-{1-[4-(4-Fluoro-phenyl)-1-oxo-2,8-diaza-spiro[4.5]dec-8-yl]-cyclohexyl}-benzonitrile As described for example 10, rac-4-(4-fluoro-phenyl)-2,8-diaza-spiro[4.5]decan-1-one (200 mg, 0.6 mmol) was converted to the title compound (16 mg, 7%) which was obtained as a white solid. MS: m/e=432.3 (M+H).

EXAMPLE 32 rac4-(4-Fluoro-phenyl)-8-[1-(4-methoxy-phenyt)-cyclohexyl]-2,8-diaza-spiro[4.5]decan-1-one As described for example 11, rac-4-(4-fluoro-phenyl)-2,8-diaza-spiro[4.5]decan-1-one (250 mg, 0.7 mmol) was converted to the title compound (95 mg, 31%) which was obtained as a white solid. MS: m/e=437.5 (M+H).

EXAMPLE 33 rac-4-(4-Fluoro-phenyl)-8-[1-(3-methoxy-phenyl)-cyclohexyl]-2,8-diaza-spiro[4.5]decan-1-one As described for example 12, rac-4-(4-fluoro-phenyl)-2,8-diaza-spiro[4.5]decan-1-one (250 mg, 0.7 mmol) was converted to the title compound (95 mg, 39%) which was obtained as a white solid. MS: m/e=437.5 (M+H).

EXAMPLE 34 rac-4-(4-Fluoro-phenyl)-8-[1-(4-trifluoromethoxy-phenyl)-cyclohexyl]-2,8-diaza-spiro[4.5]decan-1-one As described for example 14, rac-4-(4-fluoro-phenyl)-2,8-diaza-spiro[4.5]decan-1-one (200 mg, 0.6 mmol) was converted to the title compound (10 mg, 4%) which was obtained as a white solid. MS: m/e=491.5 (M+H).

EXAMPLE 35 rac-4-(4-Fluoro-phenyl)-8-[1-(3-trifluoromethoxy-phenyl)-cyclohexyl]-2,8-diaza-spiro[4.5]decan-1-one As described for example 15, rac-4-(4-fluoro-phenyl)-2,8-diaza-spiro[4.5]decan-1-one (200 mg, 0.6 mmol) was converted to the title compound (88 mg, 32%) which was obtained as a white solid. MS: m/e=491.5 (M+H).

EXAMPLE 36 rac-4-(4-Fluoro-phenyl)-8-(1-thiophen-2-yl-cyclohexyl)-2,8-diaza-spiro[4.5]decan-1-one As described for example 3, rac-4-(4-fluoro-phenyl)-2,8-diaza-spiro[4.5]decan-1-one (150 mg, 0.4 mmol) was converted to the title compound (93 mg, 53%) (using 2-iodothiophene instead of 3-iodotoluene)) which was obtained as a white solid. MS: m/e=413.4 (M+H).

EXAMPLE 37 rac-4-(4-Fluoro-phenyl)-8-[1-(5-methyl-thiophen-2-yl)-cyclohexyl]-2,8diaza-spiro[4.5]decan-1-one As described for example 3, rac-4-(4-fluoro-phenyl)-2,8-diaza-spiro[4.5]decan-1-one (100 mg, 0.28 mmol) was converted to the title compound (50 mg, 42%) (using 2-bromo-5-methylthiophene instead of 3-iodotoluene)) which was obtained as a white solid. MS: m/e=427.6 (M+H).

EXAMPLE 38 rac-4-(4-Fluoro-phenyl)-8-(1-thiophen-3-yl-cyclo-hexyl)-2,8-diaza-spiro[4.5]decan-1-one As described for example 16, rac-4-(4-fluoro-phenyl)-2,8-diaza-spiro[4.5]decan-1-one (150 mg, 0.4 mnmol) was converted to the title compound (108 mg, 62%) which was obtained as a white solid. MS: m/e=413.4 (M+H).

EXAMPLE 39 rac-4-(4-Fluoro-phenyl)-8-(1-thiazol-2-yl-cyclo-hexyl)-2,8-diaza-spiro[4.5]decan-1-one As described for example 3, rac-4-(4-fluoro-phenyl)-2,8-diaza-spiro[4.5]decan-1-one (100 mg, 0.28 mmol) was converted to the title compound (26 mg, 15%) (using 2-bromothiazole instead of 3-iodotoluene) which was obtained as a white solid. MS: m/e=414.4 (M+H).

EXAMPLE 40 rac-8-(1-Cyclopropyl-cyclohexyl)-4-(4-fluoro-phenyl)-2,8-diaza-spiro[4.5]decan-1-one As described for example 19, rac-4-(4-fluoro-phenyl)-2,8-diaza-spiro[4.5]decan-1-one (125 mg, 0.35 mmol) was converted to the title compound (11 mg, 8%) which was obtained as a light yellow solid. MS: m/e=371.3 (M+H).

EXAMPLE 41 rac-8-(1-Cyclopropyl-cyclohexyl)-4-(4-fluoro-phenyl)-2,8-diaza-spiro[4.5]decan-1-one As described for example 34, rac-4-(4-fluoro-phenyl)-2,8-diaza-spiro[4.5]decan-1-one (200 mg, 0.6 mmol) was converted to the title compound (13 mg, 6%) which was obtained as a white solid. MS: m/e=373.6 (M+H).

EXAMPLE 42 rac-8-(1-Ethyl-cyclohexyl)-4-(4-fluoro-phenyl)-2,8-diaza-spiro[4.5]decan-1-one

As described for example 3, rac-4-(4-fluoro-phenyl)-2,8-diaza-spiro[4.5]decan-1-one (200 mg, 0.6 mmol) was converted to the title compound (29 g, 14%) (using 2-iodopyridine and ethylmagnesium bromide instead of 3-iodotoluene and isopropylmagnesium chloride) which was obtained as a light brown solid. MS: m/e 359.3 (M+H).

EXAMPLE 43 rac-4-Phenyl-8-(4-phenyl-tetrahydro-pyran4-yl)-2,8-diaza-spiro [4.5]decan-1-one rac-4-(1-Oxo4-phenyl-2,8-diaza-spiro[4.5]dec-8-yl)-tetrahydro-pfran-4-carbonitrile a) As described for building block 8, rac-4-phenyl-2,8-diaza-spiro[4.5]decan-1-one (150 mg, 0.65 inmol) was converted to the title compound (70 mg, 32%) (using tetrahydro-4H-pyran-4-one instead of cyclohexanone) which was obtained as a yellow foam.
MS: m/e=340.3 (M+H).

rac-4-Phenyl-8-(4-Thenyl-tetrahydro-pfran-4-yl)-2,8-diaza-spiro[4.5]decan-1-one b) As described for example 1, rac-4-(1-oxo-4-phenyl-2,8-diaza-spiro[4.5]dec-8-yl)-tetrahydro-pyran-4-carbonitrile (70 mg, 0.2 mmol) was converted to the title compound (24 mg, 30%) which was obtained as an orange solid. MS: m/e=391.3 (M+H).

EXAMPLE 44

4-Phenyl-8-(3-phenyl-tetrahydro-pyran-3-yl)-2,8-diaza-spiro[4.5]decan-1-one rac 3-(1-Oxo-4-Phenyl-2,8-diaza-soiror4.5ldec-8-yl)-tetrahydro-poran-3-carbonitrile a) As described for example 43a, rac-4-phenyl-2,8-diaza-spiro[4.5]decan-1-one (150 mg, 0.65 mmol) was converted to the title compound (55 mg, 25%) (using dihydro-pyran-3-one instead of tetrahydro-4H-pyran-4-one) which was obtained as a white solid.
MS: m/e=340.3 (M+H).

rac4-Phenyl-8-(3T-henyl-tetrahydro-pyran-3-yl -2,8-diaza-spiro[4.5]decan-1-one b) As described for example 1, rac 3-(1-oxo-4-phenyl-2,8-diaza-spiro[4.5]dec-8-yl)-tetrahydro-pyran-3-carbonitrile (54 mg, 0.16 mmol) was converted to the title compound (20 mg, 30%) which was obtained as an orange solid. MS: m/e=391.3 (M+H).

EXAMPLE 45 rac4-(4-Fluoro-phenyl)-8-(4-phenyt-tetrahydro-thiopyran4-yl)-2,8-diaza-spiro[4.5]decan-1-one rac-4-[4-(4-Fluoro-phenyl)-1-oxo-2,8-diaza-spiro[4.5]dec-8-yl]-tetrahydro-thiopyran-4-carbonitrile a) To a stirred mixture of rac-4-(47fluoro-phenyl)-2,8-diaza-spiro[4.5]decan-1-one hydrochloride (500 mg, 2.0 mmol) and tetrahydro-4H-thiopyran-4-one (300 mg, 2.6 mmol) was added a solution of KCN (168 mg, 2.6 mmol) in water (30 mL). The resulting mixture was vigorously stirred at room temperature overnight and the resulting precipiate filtered off, washed with water and hexane and dried to afford the title compound (424 mg, 44%). MS: m/e=374.5 (M+H).

rac-4-(4-Fluoro-phenyl)-8-(4-henyl-tetrhydro-thiopyran-4-yl-2,8-diaza-spiro[4.5]decan-1-one b) As described for example 1, rac-4-[4-(4-fluoro-phenyl)-1-oxo-2,8-diaza-spiro[4.5]dec-8-yl]-tetrahydro-thiopyran-4-carbonitrile (150 mg, 0.4 mmol) was converted to the title compound (50 mg, 29%) which was obtained as a white solid. MS: mn/e=425.5 (M+H).

EXAMPLE 46 rac-4-(4-Fluoro-phenyl)-8-[4-(4-fluoro-phenyl)-tetrahydro-thiopyran-4-yl]-2,8-diaza-spiro [4.5]decan-1-one As described for example 25, rac-4-[4-(4-fluoro-phenyl)-1-oxo-2,8-diaza-spiro[4.5]dec-8-yl]-tetrahydro-thiopyran-4-carbonitrile (520 mg, 1.4 mmol) was converted to the title compound (94 mg, 15%) which was obtained as a white solid. MS: m/e=443.5 (M+H).

EXAMPLE 47 rac-8-[1-Benzyl-4-(4-fluoro-phenyl)-piperidin4-yl]-4-(4-fluoro-phenyl)-2,8-diaza-spiro[4.5]decan-1-one rac-1-Benzyl-4-[4-(4-fluoro-phenyl)-1-oxo-2,8-diaza-spiro[4.5]dec-8-yl]-piperidine-4-carbonitrile a) As described for example 43a, rac-4-(4-fluoro-phenyl)-2,8-diaza-spiro[4.5]decan-1-one (300 mg, 1.6 mmol) was converted to the title compound (650 mg, 92%) (using 1-benzyl-4-piperidone instead of cyclohexanone) which was obtained as a white solid.

MS: m/e=447.6 (M+H).

rac-8-[1-Benzyl-4-(4-fluoro-phenyl)-piperidin-4-yl]-4-(4-fluoro-ph8-yl-2-8-diaza-spiro[4.5]decan-1-one b) As described for example 25, rac-1-benzyl-4-[4-(4-fluoro-phenyl)-1-oxo-2,8-diaza-spiro[4.5]dec-8-yl]-piperidine-4-carbonitrile (500 mg, 1.1 mmol) was converted to the title compound (33 mg, 6%) which was obtained as a white solid.

MS: m/e=516.5 (M+H).

EXAMPLE 48 rac-4-Phenyl-8-(1-phenyl-cycloheptyl)-2,8-diaza-spiro[4.5]decan-1-one rac-1-[4-(Phenyl)-1-oxo-2,8-diaza-spiro[4.5]dec-8-yl]-cycloheptanecarbonitrile a) As described for example 45a, rac-4-phenyl-2,8-diaza-spiro[4.5]decan-1-one (60 mg, 0.5 mmol) was converted to the title compound (120 mg, 64%) (using cycloheptanone instead of cyclohexanone) which was obtained as a white solid. MS: m/e=352.1 (M+H).

rac-4-Phenyl-8-(1-phenyl-cycloheptyl)-2,8-diaza-spiro[4.5]decan-1-one b) As described for example 1, rac-1-[4-(phenyl)-1-oxo-2,8-diaza-spiro[4.5]dec-8-yl]-cycloheptanecarbonitrile (100 mg, 0.28 mmol) was converted to the title compound (41 mg, 36%) which was obtained as a white solid. MS: m/e=403.6 (M+H).

EXAMPLE 49 rac-4-(4-Fluoro-phenyl)-8-(1-phenyl-cycloheptyl)-2,8-diaza-spiro [4.5]decan-1-one rac-1-[4-(4-Fluoro-phenyl)-1-oxo-2,8-diaza-spiro [4.5]dec-8-yl]-cycloheptanecarbonitrile a) As described for example 48a, rac-4-(4-fluoro-phenyl)-2,8-diaza-spiro[4.5]decan-1-one (300 mg, 2.7 mmol) was converted to the title compound (488 mg, 49%) which was obtained as a white solid. MS: m/e=370.4 (M+H).

rac-4-(4-Fluoro-phenyl)-8-(1-phenyl-cycloheptyl)-2,8-diaza-spiro[4.5]decan-1-one b) As described for example 1, rac-1-[4-(4-fluoro-phenyl)-1-oxo-2,8-diaza-spiro[4.5]dec-8-yl]-cycloheptanecarbonitrile (200 mg, 0.54 mmol) was converted to the title compound (110 mg, 48%) which was obtained as a white solid. MS: m/e=421.5 (M+H).

EXAMPLE 50 rac4-(4-Fluoro-phenyl)-8-[1-(4-fluoro-phenyl)-cycloheptyl]-2,8-diaza-spiro[4.5]decan-1-one As described for example 25, rac-1-[4-(4-fluoro-phenyl)-1-oxo-2,8-diaza-spiro[4.5]dec-8-yl]-cycloheptanecarbonitrile (300 mg, 0.7 mmol) was converted to the title compound (182 mg, 77%) which was obtained as a white solid. MS: m/e=439.5 (M+H).

EXAMPLE 51 rac 8-(1-Phenyl-cyclohexyl)-4-p-tolyl-2,8-diaza-spiro [4.5]decan-1-one rac 4-(2-Nitro-1-p-tolyl-ethyl)-piperidine-1,4-dicarboxylic acid 1-tert-butyl ester 4-ethyl ester a) As described for building block 7, piperidine-1,4-dicarboxylic acid 1-tert-butyl ester 4-ethyl ester (3.15 g, 12.3 mmol) was converted to the title compound (4.86 g, 94%) (using trans-4-methyl-beta-nitrostyrene instead of 4-fluoro-trans-beta-nitrostyrene) which was obtained as a light brown foam. MS: m/e 419.4 (M−H).

rac 1-Oxo-4-ptolyl-2 8-diaza-spiro[4.5]decane-8-carboxylic acid tert-butyl ester b) As described for for building block 7, rac 4-(2-nitro-1-p-tolyl-ethyl)-piperidine-1,4-dicarboxylic acid 1-tert-butyl ester 4-ethyl ester (4.85 g, 11.5 mmol) was converted to the title compound (2.46 g, 62%) after the two-step procedure of Ra—Ni hydrogenation and heating under reflux in toluene solution. The title compound was obtained as a white solid after tritutation from pentane. MS: m/e 345.4 (M+H).

rac 4-p-Tolyl-2.8-diaza-spiro[4.5]decan-1-one c) As described for building block 7, rac 1-oxo-4-p-tolyl-2,8-diaza-spiro[4.5]decane-8-carboxylic acid tert-butyl ester (2.45 g, 7.1 mmol) was converted to the title compound (1.1 g, 63%), after treatment with TFA in DCM, which was obtained as a brown solid.

MS: m/e 245.5 (M+H).

rac 8-(1-Phenyl-cyclohexyl)-4-p-tolyl-2,8-diaza-
spiro[4.5]decan-1-one d) As described for building block 7, rac 4-p-tolyl-2,8-diaza-spiro[4.5]decan-1-one (350 mg, 0.1 mmol) was converted to the title compound (68 mg, 17%) which was obtained as an off-white solid. MS: m/e 403.5 (M+H) after the two-step procedure involving the Strecker and Bruylant reactions.

EXAMPLE 52 rac 8-[1-(4-Fluoro-phenyl)-cyclohexyl]4-p-tolyl-2,8-
diaza-spiro [4.5]decan-1-one As described for example 51, 7, rac 4-p-tolyl-2,8-diaza-spiro[4.5]decan-1-one (350 mg, 0.1 mmol) was converted to the title compound (93 mg, 22%) which was obtained as an off-white solid. MS: m/e 421.3 (M+H) after the two-step procedure involving the Strecker and Bruylant (using 4-fluorophenylmagnesium bromide instead of phenylmagnesium bromide) reactions.

EXAMPLE 53 rac 8-[1-(4-Fluoro-phenyl)-cyclohexyl]-4-(4-trifluoromethyl-phenyt)-2,8-diaza-spiro[4.5]decan-1-one rac 4-[2-Nitro-1-(4-trifluoromethl-phenyl)-ethyl]-
piperidine-1,4-dicarboxylic acid 1-tert-butyl ester
4-ethyl ester a) As described for example 51a, piperidine-1,4-dicarboxylic acid 1-tert-butyl ester 4-ethyl ester (1.71 g, 6.6 mmol) was converted to the title compound (2.05 g, 65%) (using trans-4-trifluoromethyl-beta-nitrostyrene instead of 4-fluoro-trans-beta-nitrostyrene) which was obtained as a yellow oil.

rac 1-Oxo-4-(4-trifluoromethyl-phenyl)-2,8-diaza-
spiro[4,5]decane-8-carboxylic acid tert-butyl ester b) As described for example 51b, rac 4-[2-nitro-1-(4-trifluoromethyl-phenyl)-ethyl]-piperidine-1,4-dicarboxylic acid 1-tert-butyl ester 4-ethyl ester (2.04 g, 4.3 mmol) was converted to the title compound (1.22 g, 71%) after the two-step procedure of Ra—Ni hydrogenation and heating under reflux in toluene solution containing triethylamine. The title compound was obtained as a white foam. MS: m/e 399.3 (M+H).

rac 4-(4-Trifluoromethyl-phenyl)-2,8-diaza-spiro
[4.5]decan-1-one 1:1 hydrochloride c) Rac 1-oxo-4-(4-trifluoromethyl-phenyl)-2,8-diaza-spiro[4,5]decane-8-carboxylic acid tert-butyl ester (1.22 g, 3.1 mmol) was converted to the title compound (1.03 g, 100%), after treatment with HCl in dioxane, which was obtained as a white solid.
MS: m/e 299.3 (M+H).

rac 1-[1-Oxo-4-(4-trifluoromethyl-phenyl)-2,8-
diaza-spiro[4,5]dec-8-yl]-cyclohexanecarbonitrile d) As described for example 45a, 4-(4-trifluoromethyl-phenyl)-2,8-diaza-spiro[4.5]decan-1-one 1:1 hydrochloride (974 mg, 2.9 mmol) was converted to the title compound (863 mg, 73%) which was obtained as a white solid. MS: m/e 406.3 (M+H).

rac 8-[1-(4-Fluoro-phenyl)-cyclohexyl]-4-(4-trifluoromethyl-phenyl)-2,8-diaza-spiro[4.5]decan-1-one e) As described for example 25, 7, rac 1-[1-oxo-4-(4-trifluoromethyl-phenyl)-2,8-diaza-spiro[4.5]dec-8-yl]-cyclohexanecarbonitrile (250 mg, 0.62 mmol) was converted to the title compound (34 mg, 12%) which was obtained as a white solid.
MS m/e 475.1 (M+H).

EXAMPLE 54 rac 8-[1-(4-Fluoro-phenyl)-cyclohexyl]-4-(4-methoxy-phenyl)-2,8-diaza-spiro[4.5]decan-1-one rac 4-[1-(4-MethoxU-phenyl)-2-nitro-ethyl]-piperidine-14-dicarboxylic acid 1-tert-butyl ester 4-ethyl
ester a) As described for example 51a, piperidine-1,4-dicarboxylic acid 1-tert-butyl ester 4-ethyl ester (2.87 g, 78 mmol) was converted to the title compound (3.8 g, 78%) (using 1-(4-methoxyphenyl)-2 nitroethene instead of 4-fluoro-trans-beta-nitrostyrene) which was obtained as a light brown foam. MS: m/e 437.6 (M+H).

rac 4-(4-Methoxy-phenyl)-1-oxo-2,8-diaza-spiro
[4.5]decane-8-carboxylic acid tert-butyl ester b) As described for example 51b, 4-[1-(4-methoxy-phenyl)-2-nitro-ethyl]-piperidine-1,4-dicarboxylic acid 1-tert-butyl ester 4-ethyl ester (3.8 g, 8.7 mmol) was converted to the title compound (750 mg, 21%) after the two-step procedure of Ra—Ni hydrogenation and heating under reflux in toluene solution containing triethylamine. The title compound was obtained as a white foam. MS: m/e 361.6 (M+H).

rac 4-(4-Methoxy-phenyl)-2
8-diaza-spiro[4.5]decan-1-one c) As described for example 51c, rac 4-(4-methoxy-phenyl)-1-oxo-2,8-diaza-spiro[4.5]decane-8-carboxylic acid tert-butyl ester (0.74 g, 2.1 mmol) was converted to the title compound (328 mg, 61%), after treatment with TFA in DCM, which was obtained as a white solid. MS: m/e 261.3 (M+H).

rac 1-[4-(4-Methoxy-phenyl)-1-oxo-2,8-diaza-spiro
[4.5]dec-8-yl]-cyclohexanecarbonitrile d) As described for example 45a, 4-(4-methoxy-phenyl)-2,8-diaza-spiro[4.5]decan-1-one (300 mg, 1.2 mmol) was converted to the title compound (270 mg, 64%) which was obtained as a white solid. MS: mn/e 368.4 (M+H).

rac 8-[1-(4-Fluoro-phenyl)-cyclohexyl]-4-(4-methoxy-nhen 1)-2 8-diaza-spiro[4.5]decan-1-one e) As described for example 25, rac 1-[4-(4-methoxy-phenyl)-1-oxo-2,8-diaza-spiro[4.5]dec-8-yl]-cyclohexanecarbonitrile (250 mg, 0.68 mmol) was converted to the title compound (104 mg, 35%) which was obtained as a white solid.
MS: m/e 437.4 (M+H).

EXAMPLE 55 rac 8-(1-Phenyl-cyclohexyl)-4-thiophen-2-yl-2,8-diaza-spiro[4.5]decan-1-one rac 4-(2-Nitro-1-thiophen-2-yl-ethyl)-piperidine-14-dicarboxylic acid 1-tert-butyl ester 4-ethyl ester a) As described for example 51a, piperidine-1,4-dicarboxylic acid 1-tert-butyl ester 4-ethyl ester (1.66 g, 10.7 mmol) was converted to the title compound (1.62 g, 61%) (using 2-(2-nitrovinyl)thiophene instead of 4-fluoro-trans-beta-nitrostyrene) which was obtained as a dark brown solid. MS: m/e 413.4 (M+H).

rac 4-(2-Amnino-1-thiophen-2-yl-ethyl)-piperidine-1,4-dicarboxylic acid 1-tert-butyl ester 4-ethyl ester b) To a solution of 4-(2-nitro-1-thiophen-2-yl-ethyl)-piperidine-1,4-dicarboxylic acid 1-tert-butyl ester 4-ethyl ester (1.5 g, 3.6 mnnol) in acetic acid (15 mL) was added Zinc dust (2 g, 30.6 mmol) and the resulting mixture stirred at room temperature for 3 h. The mixture was then diluted with water and basufied with sodium carbonate. The product was extracted with ethyl acetate and the combined organic extracts were then washed with brine, dried over sodium sulfate, filtered and evaporated. Purification by chromatography on silica gel eluting with DCM: MeOH (98:2) afforded the title compound (403 mg, 29%) as a light brown foam. MS: me=399.5 (M+NH$_4$).

rac 8-(1-Phenyl-cyclohexyl)-4-thiophen-2-yl-2,8-diaza-spiro[4.5]decan-1-one c) A mixture of 4-(2-amino-1-thiophen-2-yl-ethyl)-piperidine-1,4-dicarboxylic acid 1-tert-butyl ester 4-ethyl ester (400 mg, 0.97 mmol) in toluene (3 mL) containing triethylamine (0.2 mL) was heated under reflux for 5 h. After cooling to room temperature the mixture was evaporated to afford the cyclic amide
[MS: m/e 337.3 (M+H)]which was was then dissolved in dicloromethane (4 mL) and trifluoro acetic acid (0.8 mL, 1.1 mmol) was added and the resulting mixture stirred at room temperature for 30 min. The mixture was then basified with NaOH (2 N) in the product extracted with dicloromethane to affor the amine (76 mg, 30%) as a brown foam. This product was then treated in an analogous manner to example 45a to afford the Strecker product (75 mg, 69%) as a brown oil. MS: m/e=344.3 (M+H). This product was then treated as described for example 1, to afford the title compound (42 mg, 52%) which was obtained as a light yellow oil. MS: m/e 395.3 (M+H).

EXAMPLE 56 rac 8-(1-Phenyl-cyclohexyl)4-propyl-2,8-diaza-spiro[4.5]decan-1-one

1-Nitro-pent-1-ene a) To a solution of butyraldehyde (90.1 mL, 1 mol) in aquesous NaHSO$_3$ (38%, 207.5 nL, 1 mol) and water (293 mL) was added a solution of nitromethane (54.1 mL, 1 mol) dissolved in NaOH (2 N, 150 mL, 300 mmol) and water (50 mL) and the resulting mixture stirred at 43° C. for 3 h and then heated under reflux for 30 min. The mixture was then cooled to room temperature overnight and adjusted to pH~4 with HCl (6 N). The product was extracted with diethyl ether (3×500 mL) and the combined organic layers where then washed with H$_2$O and brine, dried over sodium sulfate and evaporated to leave a brown liquid (37.6 g, 282 mmol). This product was then dissolved in chloroform (100 mL) and treated with acetyl chloride (23 mL, 325 rumol) and the resulting mixture stirred at room temperature for 3 h and then heated under reflux for 30 min. After cooling to room temperature the mixture was poured onto ice and neutralized with solid NaHCO$_3$. The product was extracted with chloroform (2×200 mL) and the combined organic layers where then washed with H$_2$O and brine, dried over sodium sulfate and evaporated to leave a brown liquid (46.1 g, 263 mmol). This product was then dissolved in ethyl acetate (1 L) and then sodium acetate (69.1 g, 842 mmol) added and the resulting mixture stirred at room temperature for 48 h. The mixture was then filtered and the solution evaporated. The residue was then partioned between diethyl ether and water and the water layer extracted with diethyl ether. The combined organic layers where then washed with H$_2$O and brine, dried over sodium sulfate and evaporated to leave a brown liquid (46 g). The title compound (6.8 g, 23%) was purified by steam distillation (bp 70° C. at 8 torr).

rac 4-(1-Nitromethyl-butyl)-piperidine-1,4-dicarboxylic acid 1-tert-butyl ester 4-ethyl ester b) As described for building block 7, piperidine-1,4-dicarboxylic acid 1-tert-butyl ester 4-ethyl ester (15.3 g, 59 mmol) was converted to the title compound (21.2 g, 96%) (using 1-nitro-pent-1-ene instead of 4-fluoro-trans-beta-nitrostyrene) which was obtained as a yellow oil. MS: m/e 371.2 (M–H).

rac 1-Oxo-4-propyl-2,8-diaza-spiro[4.5]decane-8-carboxylic acid tert-butyl ester c) As described for for building block 7, rac 4-(1-nitromethyl-butyl)-piperidine-1,4-dicarboxylic acid 1-tert-butyl ester 4-ethyl ester (21.2 g, 57 mmol) was converted to the title compound (11.2 g, 66%) after the two-step procedure of Ra—Ni hydrogenation and heating under reflux in toluene solution. The title compound was obtained as a white solid after tritutation from hot pentane. MS: m/e 297.5 (M+H).

rac 4-Propyl-2,8-diaza-spiro[4.5]decan-1-one d) As described for building block 7, 1-oxo-4-propyl-2,8-diaza-spiro[4.5]decane-8-carboxylic acid tert-butyl ester (11.2 g, 38 mmol) was converted to the title compound (6.3 g, 85%) which was obtained as a light yellow liquid. MS: m/e 197.4 (M+H).

rac 1-(1-Oxo-4-propyl-2,8-diaza-sMiro[4.5]dec-8-yl)-cyclohexanecarbonitrile e) As described for building block 8, rac 4-propyl-2,8-diaza-spiro[4.5]decan-1-one (4.0 g, 20 mmol) was converted to the title compound (718 mg, 12%) which was obtained as a white solid. MS: m/e 304.4 (M+H).

rac 8-(1-Phenyl-cyclohexyl)-4-propyl-2,8-diaza-spiro[4.5]decan-1-one

As described for example 1, 1-(1-oxo-4-propyl-2,8-diaza-spiro[4.5]dec-8-yl)-cyclohexanecarbonitrile (200 mg, 0.66 mmol) was converted to the title compound (122 mg, 52%) which was obtained as a white solid. MS: m/e 355.5 (M+H).

EXAMPLE 57 rac 8-[1-(4-Fluoro-phenyl)-cyclohexyl]-4-propyl-2,8-diaza-spiro[4.5]decan-1-one

As described for example 25, rac 1-(1-oxo-4-propyl-2,8-diaza-spiro[4.5]dec-8-yl)-cyclohexanecarbonitrile (200 mg, 0.66 mmol) was converted to the title compound (87 mg, 35%) which was obtained as a white solid. MS: m/e 373.5 (M+H).

EXAMPLE 58 rac 4-Propyl-8-(1-thiophen-2-yl-cyclohexyl)-2,8-diaza-spiro[4.5]decan-1-one

As described for example 36, rac 1-(1-oxo-4-propyl-2,8-diaza-spiro[4.5]dec-8-yl)-cyclohexanecarbonitrile (75 mg, 0.3 mmol) was converted to the title compound (40 mg, 45%) which was obtained as a white solid. MS: m/e 361.5 (M+H).

EXAMPLE 59 rac 8-[1-(5-Methyl-thiophen-2-yl)-cyclohexyl]-4-propyl-2,8-diaza-spiro[4.5]decan-1-one As described for example 37, rac 1-(1-oxo-4-propyl-2,8-diaza-spiro[4.5]dec-8-yl)-cyclohexanecarbonitrile (77 mg, 0.3 mmol) was converted to the title compound (29 mg, 31%) which was obtained as a white solid. MS: m/e 375.4 (M+H).

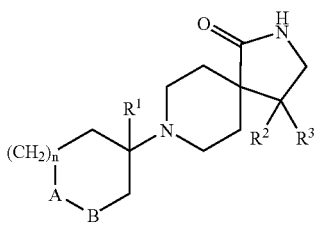

| n | A-B | R¹ | R³ | R² | Example |
|---|---|---|---|---|---|
| 1 | CH₂CH₂ | 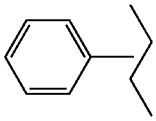 | H | 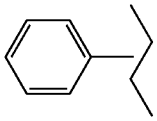 | 1 |
| 1 | CH₂CH₂ | 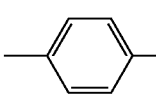 | H | 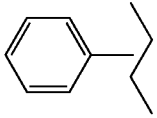 | 2 |
| 1 | CH₂CH₂ | 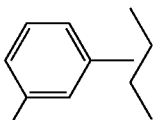 | H | 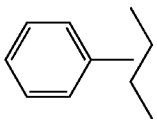 | 3 |
| 1 | CH₂CH₂ | 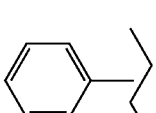 | H | 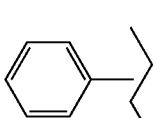 | 4 |
| 1 | CH₂CH₂ | 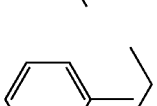 | H | 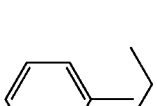 | 5 |

-continued
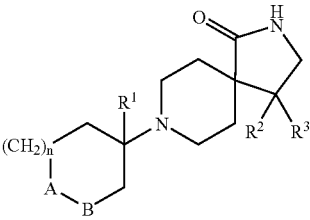
| n | A-B | R¹ | R³ | R² | Example |
|---|---|---|---|---|---|
| 1 | CH₂CH₂ | 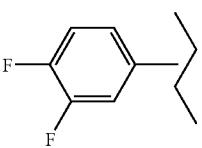 | H | 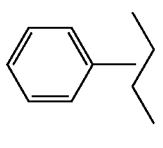 | 6 |
| 1 | CH₂CH₂ | 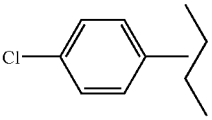 | H | 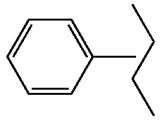 | 7 |
| 1 | CH₂CH₂ | 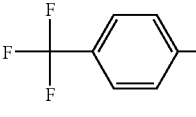 | H | 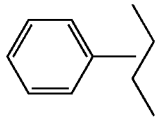 | 8 |
| 1 | CH₂CH₂ | 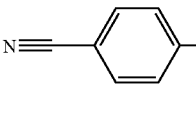 | H | 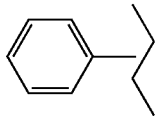 | 9 |
| 1 | CH₂CH₂ | 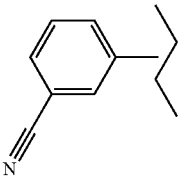 | H | 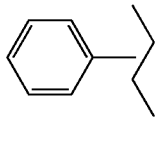 | 10 |
| 1 | CH₂CH₂ | 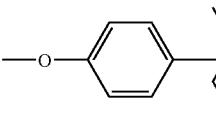 | H | 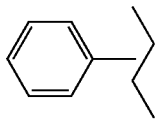 | 11 |
| 1 | CH₂CH₂ | 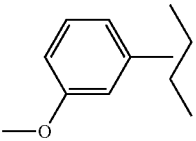 | H | 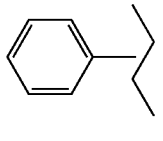 | 12 |
| 1 | CH₂CH₂ | 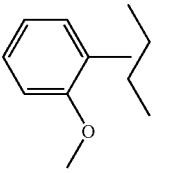 | H | 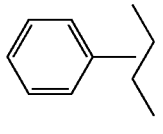 | 13 |

-continued

| n | A-B | R¹ | R³ | R² | Example |
|---|---|---|---|---|---|
| 1 | CH₂CH₂ | 4-(trifluoromethoxy)phenyl-CH₂CH(CH₃)- | H | phenyl-CH₂CH(CH₃)- | 14 |
| 1 | CH₂CH₂ | 3-(trifluoromethoxy)phenyl-CH₂CH(CH₃)- | H | phenyl-CH₂CH(CH₃)- | 15 |
| 1 | CH₂CH₂ | thiophen-3-yl-CH₂CH(CH₃)- | H | phenyl-CH₂CH(CH₃)- | 16 |
| 1 | CH₂CH₂ | cyclohexyl-CH₂CH(CH₃)- | H | phenyl-CH₂CH(CH₃)- | 17 |
| 1 | CH₂CH₂ | cyclopentyl-CH₂CH(CH₃)- | H | phenyl-CH₂CH(CH₃)- | 18 |
| 1 | CH₂CH₂ | cyclopropyl-CH₂CH(CH₃)- | H | phenyl-CH₂CH(CH₃)- | 19 |
| 1 | CH₂CH₂ | (CH₃)₂CHCH₂CH(CH₃)- | H | phenyl-CH₂CH(CH₃)- | 20 |
| 1 | CH₂CH₂ | (CH₃)₂C=CHCH₂CH(CH₃)- | H | phenyl-CH₂CH(CH₃)- | 21 |
| 1 | CH₂CH₂ | 4-methylphenyl-CH₂CH(CH₃)- | H | 4-fluorophenyl-CH₂CH(CH₃)- | 22 |

-continued
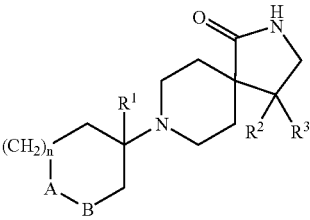
| n | A-B | R¹ | R³ | R² | Example |
|---|-----|----|----|----|---------|
| 1 | CH₂CH₂ | 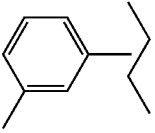 | H | 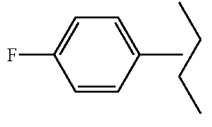 | 23 |
| 1 | CH₂CH₂ | 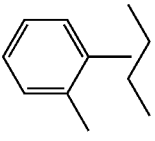 | H | 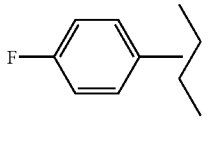 | 24 |
| 1 | CH₂CH₂ | 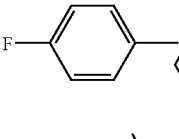 | H | 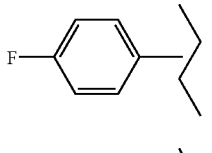 | 25 |
| 1 | CH₂CH₂ | 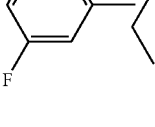 | H | 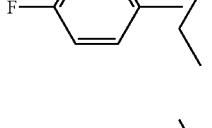 | 26 |
| 1 | CH₂CH₂ | 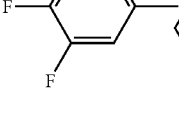 | H | 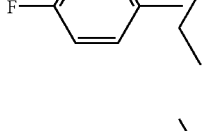 | 27 |
| 1 | CH₂CH₂ | 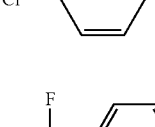 | H | 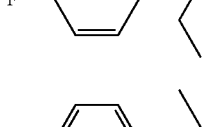 | 28 |
| 1 | CH₂CH₂ | 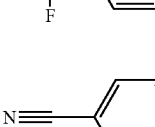 | H | 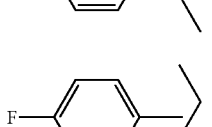 | 29 |
| 1 | CH₂CH₂ | 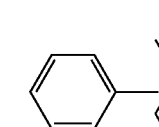 | H | 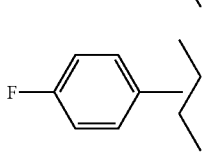 | 30 |
| 1 | CH₂CH₂ |  | H |  | 31 |

-continued
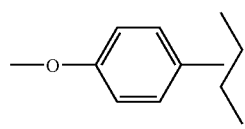
| n | A-B | R¹ | R³ | R² | Example |
|---|-----|-----|----|----|---------|
| 1 | CH₂CH₂ | 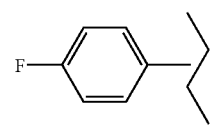 | H | 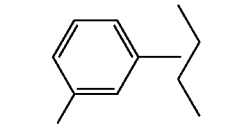 | 32 |
| 1 | CH₂CH₂ | 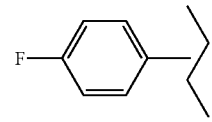 | H | 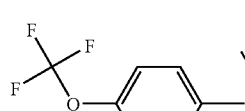 | 33 |
| 1 | CH₂CH₂ | 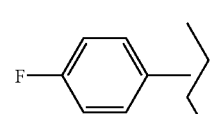 | H | 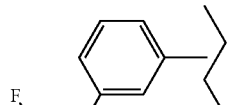 | 34 |
| 1 | CH₂CH₂ | 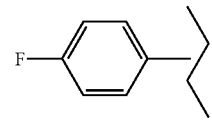 | H | 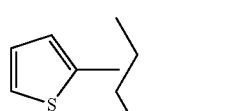 | 35 |
| 1 | CH₂CH₂ | 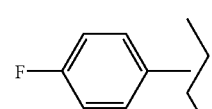 | H | 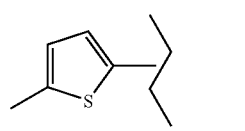 | 36 |
| 1 | CH₂CH₂ | 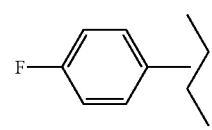 | H | 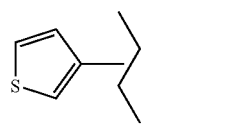 | 37 |
| 1 | CH₂CH₂ | 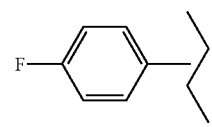 | H | 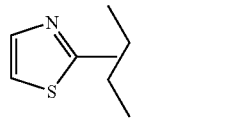 | 38 |
| 1 | CH₂CH₂ | 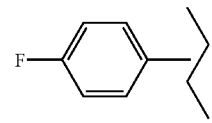 | H | 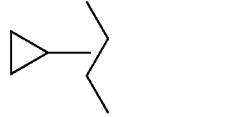 | 39 |
| 1 | CH₂CH₂ | 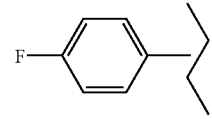 | H |  | 40 |

-continued
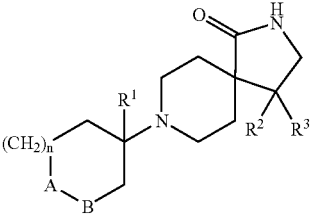
| n | A-B | R¹ | R³ | R² | Example |
|---|-----|-----|-----|-----|---------|
| 1 | CH₂CH₂ | 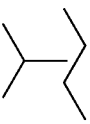 | H | 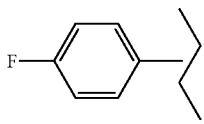 | 41 |
| 1 | CH₂CH₂ | 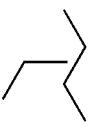 | H | 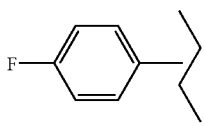 | 42 |
| 1 | OCH₂ |  | H | 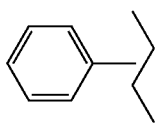 | 43 |
| 1 | CH₂O | 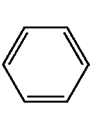 | H | 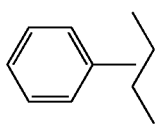 | 44 |
| 1 | SCH₂ |  | H | 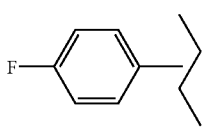 | 45 |
| 1 | SCH₂ | 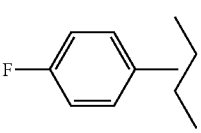 | H | 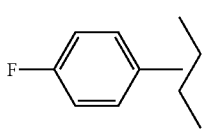 | 46 |
| 1 | BnNCH₂ | 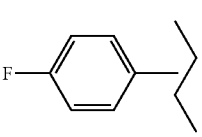 | H | 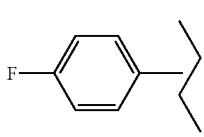 | 47 |
| 2 | CH₂CH₂ |  | H | 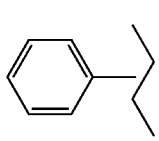 | 48 |
| 2 | CH₂CH₂ |  | H | 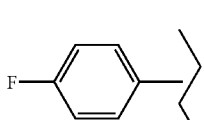 | 49 |

-continued
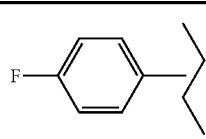
| n | A-B | R¹ | R³ | R² | Example |
|---|---|---|---|---|---|
| 2 | CH₂CH₂ | 4-F-C₆H₄-CH(CH₃)- | H | 4-F-C₆H₄-CH(CH₃)- | 50 |
| 1 | CH₂CH₂ | C₆H₅-CH(CH₃)- | H | C₆H₅-CH(CH₃)- | 51 |
| 1 | CH₂CH₂ | 4-F-C₆H₄-CH(CH₃)- | H | C₆H₅-CH(CH₃)- | 52 |
| 1 | CH₂CH₂ | 4-F-C₆H₄-CH(CH₃)- | H | 4-CF₃-C₆H₄-CH(CH₃)- | 53 |
| 1 | CH₂CH₂ | 4-F-C₆H₄-CH(CH₃)- | H | 4-MeO-C₆H₄-CH(CH₃)- | 54 |
| 1 | CH₂CH₂ | C₆H₅-CH(CH₃)- | H | 2-thienyl-CH(CH₃)- | 55 |
| 1 | CH₂CH₂ | C₆H₅-CH(CH₃)- | H | sec-butyl | 56 |
| 1 | CH₂CH₂ | 4-F-C₆H₄-CH(CH₃)- | H | sec-butyl | 57 |
| 1 | CH₂CH₂ | 2-thienyl-CH(CH₃)- | H | sec-butyl | 58 |

-continued

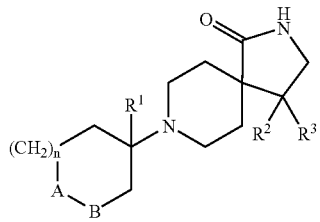

| n | A-B | R¹ | R³ | R² | Example |
|---|---|---|---|---|---|
| 1 | CH₂CH₂ | (5-methylthiophen-2-yl methyl-propyl group) | H | (branched pentyl) | 59 |

Tablet Formulation (Wet Granulation)

| | | mg/tablet | | |
|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | |
|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The invention claimed is:

1. A compound of the formula I

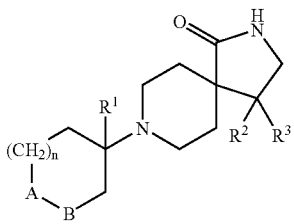

I wherein
A-B is $CH_2$—$CH_2$, —$CH_2$—O—, —O—$CH_2$—, —$CH_2$—S—, —S—$CH_2$—, —$CH_2$—C(O)—, —C(O)—$CH_2$—, —N($R^4$)—$CH_2$— or —$CH_2$—N($R^4$)—;
$R^1$ is lower alkyl, lower alkenyl, cycloalkyl, or is aryl, optionally substituted by one or two substituents selected from the group consisting of halogen, cyano, lower alkyl, $CF_3$, $OCF_3$ and lower alkoxy, or is heteroaryl, optionally substituted by one or two substituents selected from the group consisting of halogen, lower alkyl, $CF_3$ and lower alkoxy;
$R^2$ is lower alkyl, cycloalkyl, or is aryl, optionally substituted by one or two substituents selected from the group consisting of halogen, lower alkyl, $CF_3$, and lower alkoxy, or
is heteroaryl, optionally substituted by one or two substituents selected from the group consisting of halogen, lower alkyl, $CF_3$ and lower alkoxy;
$R^3$ is hydrogen, lower alkyl or benzyl;
$R^4$ is hydrogen or benzyl; and
n is 0, 1 or 2;
or a pharmaceutically acceptable salt thereof.

2. A compound of formula I according to claim 1

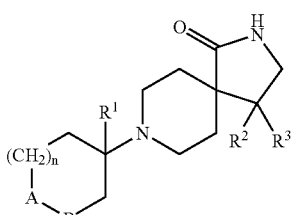

I wherein
A-B is —CH₂—CH₂—, —CH₂—O—, —O—CH₂—, —S—CH₂— or —N(R⁴)—CH₂—;
R¹ is lower alkyl, lower alkenyl, cycloalkyl, or is phenyl, optionally substituted by one or two substituents selected from the group consisting of halogen, cyano, lower alkyl, CF₃, OCF₃ and lower alkoxy, or is heteroaryl, optionally substituted by lower alkyl;
R² is lower alkyl, or is phenyl, optionally substituted by one substituent selected from the group consisting of halogen, lower alkyl, CF₃, and lower alkoxy, or is heteroaryl;
R³ is hydrogen;
R⁴ is benzyl; and
n is 1 or 2;
or a pharmaceutically acceptable salt thereof.

3. A compound of formula I according to claim 1, wherein n is 1.

4. A compound of formula I according to claim 3, wherein —A-B— is —CH₂—CH₂—.

5. A compound of formula I according to claim 4, wherein R¹ is phenyl, optionally substituted by halogen or lower alkyl.

6. A compound of formula I according to claim 5, wherein R² is phenyl.

7. A compound of formula I according to claim 6, selected from the group consisting of
rac-4-Phenyl-8-(1-phenyl-cyclohexyl)-2,8-diaza-spiro[4.5]decan-1-one;
rac-4-Phenyl-8-(1-p-tolyl-cyclohexyl)-2,8-diaza-spiro[4.5]decan-1-one;
rac-4-Phenyl-8-(1-m-tolyl-cyclohexyl)-2,8-diaza-spiro[4.5]decan-1-one;
rac-4-Phenyl-8-(1-o-tolyl-cyclohexyl)-2,8-diaza-spiro[4.5]decan-1-one;
rac-8-[1-(3-Fluoro-phenyl)-cyclohexyl]-4-phenyl-2,8-diaza-spiro[4.5]decan-1-one;
rac-8-[1-(3,4-Difluoro-phenyl)-cyclohexyl]-4-phenyl-2,8-diaza-spiro[4.5]decan-1-one;
rac-8-[1-(4-Chloro-phenyl)-cyclohexyl]-4-phenyl-2,8-diaza-spiro[4.5]decan-1-one; and
rac-4-Phenyl-8-[1-(4-trifluoromethyl-phenyl)-cyclohexyl]-2,8-diaza-spiro[4.5]decan-1-one.

8. A compound of formula I according to claim 5, wherein R² is phenyl substituted by halogen or alkyl.

9. A compound of formula I according to claim 8, selected from the group consisting of
rac-4-(4-Fluoro-phenyl)-8-(1-p-tolyl-cyclohexyl)-2,8-diaza-spiro[4.5]decan-1-one;
rac-4-(4-Fluoro-phenyl)-8-(1-m-tolyl-cyclohexyl)-2,8-diaza-spiro[4.5]decan-1-one;
rac-4-(4-Fluoro-phenyl)-8-(1-o-tolyl-cyclohexyl)-2,8-diaza-spiro[4.5]decan-1-one;
rac-4-(4-Fluoro-phenyl)-8-[1-(4-fluoro-phenyl)-cyclohexyl]-2,8-diaza-spiro[4.5]decan-1-one;
rac-4-(4-Fluoro-phenyl)-8-[1-(3-fluoro-phenyl)-cyclohexyl]-2,8-diaza-spiro[4.5]decan-1-one;
rac-8-[1-(3,4-Difluoro-phenyl)-cyclohexyl]-4-(4-fluoro-phenyl)-2,8-diaza-spiro[4.5]decan-1-one;
rac-8-[1-(4-Chloro-phenyl)-cyclohexyl]-4-(4-fluoro-phenyl)-2,8-diaza-spiro[4.5]decan-1-one;
rac-4-(4-Fluoro-phenyl)-8-[1-(4-trifluoromethyl-phenyl)-cyclohexyl]-2,8-diaza-spiro[4.5]decan-1-one;
rac 8-(1-Phenyl-cyclohexyl)-4-p-tolyl-2,8-diaza-spiro[4.5]decan-1-one;
rac 8-[1-(4-Fluoro-phenyl)-cyclohexyl]-4-p-tolyl-2,8-diaza-spiro[4.5]decan-1-one; and
rac 8-[1-(4-Fluoro-phenyl)-cyclohexyl]-4-(4-trifluoromethyl-phenyl)-2,8-diaza-spiro[4.5]decan-1-one.

10. A compound of formula I according to claim 5, wherein R² is phenyl substituted by alkoxy.

11. A compound of formula according to claim 10, which is
rac 8-[1-(4-Fluoro-phenyl)-cyclohexyl]-4-(4-methoxy-phenyl)-2,8-diaza-spiro[4.5]decan-1-one.

12. A compound of formula I according to claim 4, wherein R¹ is thiophenyl and R² is phenyl substituted by halogen.

13. A compound of formula I according to claim 12, selected from the group consisting of
rac-4-Phenyl-8-(1-thiophen-3-yl-cyclohexyl)-2,8-diaza-spiro[4.5]decan-1-one;
rac-4-(4-Fluoro-phenyl)-8-(1-thiophen-2-yl-cyclohexyl)-2,8-diaza-spiro[4.5]decan-1-one;
rac-4-(4-Fluoro-phenyl)-8-[1-(5-methyl-thiophen-2-yl)-cyclohexyl]-2,8-diaza-spiro[4.5]decan-1-one; and
rac-4-(4-Fluoro-phenyl)-8-(1-thiophen-3-yl-cyclohexyl)-2,8-diaza-spiro[4.5]decan-1-one.

14. A compound of formula I according to claim 4, wherein R² is lower alkyl.

15. A compound of formula I according to claim 14, wherein R¹ is phenyl.

16. A compound of formula I according to claim 15, selected from the group consisting of
rac 8-(1-Phenyl-cyclohexyl)-4-propyl-2,8-diaza-spiro[4.5]decan-1-one and
rac 8-[1-(4-Fluoro-phenyl)-cyclohexyl]-4-propyl-2,8-diaza-spiro[4.5]decan-1-one.

17. A compound of formula I according to claim 14, wherein R¹ is thiophenyl optionally substituted by alkyl.

18. A compound of formula I according to claim 17, selected from the group consisting of
rac 4-Propyl-8-(1-thiophen-2-yl-cyclohexyl)-2,8-diaza-spiro[4.5]decan-1-one and
rac 8-[1-(5-Methyl-thiophen-2-yl)-cyclohexyl]-4-propyl-2,8-diaza-spiro[4.5]decan-1-one.

19. A compound of formula I according to claim 4, wherein R¹ is phenyl substituted by cyano.

20. A compound of formula I according to claim 19, selected from the group consisting of
rac-4-[1-(1-Oxo-4-phenyl-2,8-diaza-spiro[4.5]dec-8-yl)-cyclohexyl]-benzonitrile;
rac-3-[1-(1-Oxo-4-phenyl-2,8-diaza-spiro[4.5]dec-8-yl)-cyclohexyl]-benzonitrile;
rac-4-{1-[4-(4-Fluoro-phenyl)-1-oxo-2,8-diaza-spiro[4.5]dec-8-yl]-cyclohexyl}-benzonitrile; and
rac-3-{1-[4-(4-Fluoro-phenyl)-1-oxo-2,8-diaza-spiro[4.5]dec-8-yl]-cyclohexyl}-benzonitrile.

21. A compound of formula I according to claim 4, wherein R¹ is phenyl substituted by lower alkoxy or OCF₃.

22. A compound of formula I according to claim 21, selected from the group consisting of
rac-8-[1-(4-Methoxy-phenyl)-cyclohexyl]-4-phenyl-2,8-diaza-spiro[4.5]decan-1-one;
rac-8-[1-(3-Methoxy-phenyl)-cyclohexyl]-4-phenyl-2,8-diaza-spiro[4.5]decan-1-one;
rac-8-[1-(2-Methoxy-phenyl)-cyclohexyl]-4-phenyl-2,8-diaza-spiro[4.5]decan-1-one;
rac-4-Phenyl-8-[1-(4-trifluoromethoxy-phenyl)-cyclohexyl]-2,8-diaza-spiro[4.5]decan-1-one;
rac-4-Phenyl-8-[1-(3-trifluoromethoxy-phenyl)-cyclohexyl]-2,8-diaza-spiro[4.5]decan-1-one;
rac-4-(4-Fluoro-phenyl)-8-[1-(4-methoxy-phenyl)-cyclohexyl]-2,8-diaza-spiro[4.5]decan-1-one;

rac-4-(4-Fluoro-phenyl)-8-[1-(3-methoxy-phenyl)-cyclohexyl]-2,8-diaza-spiro[4.5]decan-1-one;

rac-4-(4-Fluoro-phenyl)-8-[1-(4-trifluoromethoxy-phenyl)-cyclohexyl]-2,8-diaza-spiro[4.5]decan-1-one; and rac-4-(4-Fluoro-phenyl)-8-[1-(3-trifluoromethoxy-phenyl)-cyclohexyl],-2,8-diaza-spiro[4.5]decan-1-one.

23. A compound of formula I according to claim 4, wherein $R^1$ is lower alkyl or lower alkenyl.

24. A compound of formula I according to claim 23, selected from the group consisting of rac-8-(1-Isopropyl-cyclohexyl)-4-phenyl-2,8-diaza-spiro[4.5]decan-1-one;

rac 8-[1-(2-Methyl-propenyl)-cyclohexyl]-4-phenyl-2,8-diaza-spiro[4.5]decan-1-one;

rac-8-(1-Cyclopropyl-cyclohexyl)-4-(4-fluoro-phenyl)-2,8-diaza-spiro[4.5]decan-1-one; and rac-8-(1-Ethyl-cyclohexyl)-4-(4-fluoro-phenyl)-2,8-diaza-spiro [4.5]decan-1-one.

25. A compound of formula I according to claim 4, wherein $R^1$ is cycloalkyl.

26. A compound of formula I according to claim 25, selected from the group consisting of rac-8-Bicyclohexyl-1-yl-4-phenyl-2,8-diaza-spiro[4.5]decan-1-one;

rac-8-(1-Cyclopentyl-cyclohexyl)-4-phenyl-2,8-diaza-spiro[4.5]decan-1-one;

rac-8-(1-Cyclopropyl-cyclohexyl)-4-phenyl-2,8-diaza-spiro[4.5]decan-1-one; and rac-8-(1-Cyclopropyl-cyclohexyl)-4-(4-fluoro-phenyl)-2,8-diaza-spiro[4.5]decan-1-one.

27. A compound of formula I according to claim 4, wherein $R^1$ is thiophenyl optionally substituted by lower alkyl.

28. A compound of formula I according to claim 27, which is rac 8-(1-Phenyl-cyclohexyl)-4-thiophen-2-yl-2,8-diaza-spiro[4.5]decan-1-one.

29. A compound of formula I according to claim 4, wherein $R^1$ is heteroaryl optionally substituted by lower alkyl.

30. A compound of formula I according to claim 29, which is rac-4-(4-Fluoro-phenyl)-8-(1-thiazol-2-yl-cyclohexyl)-2,8-diaza-spiro[4.5]decan-1-one.

31. A compound of formula I according to claim 1, wherein —A-B— is —O—CH$_2$—.

32. A compound of formula I according to claim 31, which is rac-4-Phenyl-8-(4-phenyl-tetrahydro-pyran-4-yl)-2,8-diaza-spiro[4.5]decan-1-one.

33. A compound of formula I according to claim 1, wherein —A-B— is CH$_2$—O—.

34. A compound of formula I according to claim 33, which is

4-Phenyl-8-(3-phenyl-tetrahydro-pyran-3-yl)-2,8-diaza-spiro[4.5]decan-1-one.

35. A compound of formula I according to claim 1, wherein —A-B— is —S—CH$_2$—.

36. A compound of formula I according to claim 35, selected from the group consisting of rac-4-(4-Fluoro-phenyl)-8-(4-phenyl-tetrahydro-thiopyran-4-yl)-2,8-diaza-spiro[4.5]decan-1-one and rac-4-(4-Fluoro-phenyl)-8-[4-(4-fluoro-phenyl)-tetrahydro-thiopyran-4-yl]-2,8-diaza-spiro[4.5]decan-1-one.

37. A compound of formula I according to claim 1, wherein —A-B— is —N(benzyl)—CH$_2$—.

38. A compound of formula I according to claim 37, which is rac-8-[1-Benzyl-4-(4-fluoro-phenyl)-piperidin-4-yl]-4-(4-fluoro-phenyl)-2,8-diaza-spiro[4.5]decan-1-one.

39. A compound of formula I according to claim 1, wherein n is 2.

40. A compound of formula I according to claim 39, selected from the group consisting of rac-4-Phenyl-8-(1-phenyl-cycloheptyl)-2,8-diaza-spiro[4.5]decan-1-one;

rac-4-(4-Fluoro-phenyl)-8-(1-phenyl-cycloheptyl)-2,8-diaza-spiro[4.5]decan-1-one; and rac-4-(4-Fluoro-phenyl)-8-[1-(4-fluoro-phenyl)-cycloheptyl]-2,8-diaza-spiro[4.5]decan-1-one.

41. A pharmaceutical composition comprising a therapeutically effective amount of one or more compounds of formula I wherein A-B is CH$_2$—CH$_2$, —CH$_2$—O—, —O—CH$_2$—, —CH$_2$—S—, —S—CH$_2$—, —CH$_2$—C(O)—, —C(O)—CH$_2$—, —N(R$^4$)—CH$_2$— or —CH$_2$—N(R$^4$)—;

$R^1$ is lower alkyl, lower alkenyl, cycloalkyl, or is aryl, optionally substituted by one or two substituents selected from the group consisting of halogen, cyano, lower alkyl, CF$_3$, OCF$_3$ and lower alkoxy, or is heteroaryl, optionally substituted by one or two substituents selected from the group consisting of halogen, lower alkyl, CF$_3$ and lower alkoxy;

$R^2$ is lower alkyl, cycloalkyl, or is aryl, optionally substituted by one or two substituents selected from the group consisting of halogen, lower alkyl, CF$_3$, and lower alkoxy, or is heteroaryl, optionally substituted by one or two substituents selected from the group consisting of halogen, lower alkyl, CF$_3$ and lower alkoxy;

$R^3$ is hydrogen, lower alkyl or benzyl;

$R^4$ is hydrogen or benzyl;

n is 0, 1 or 2;

or a pharmaceutically acceptable salt thereof and a pharmaceutically acceptable carrier.

* * * * *